(12) United States Patent
Zitvogel et al.

(10) Patent No.: US 12,246,044 B2
(45) Date of Patent: Mar. 11, 2025

(54) BACTERIAL AND CELL COMPOSITIONS FOR THE TREATMENT OF COLORECTAL CANCER AND METHODS FOR ASSESSING A PROGNOSIS FOR PATIENTS HAVING THE SAME

(71) Applicant: INSTITUT GUSTAVE ROUSSY, Villejuif (FR)

(72) Inventors: Laurence Zitvogel, Paris (FR); Maria Paula Roberti, Paris (FR)

(73) Assignee: INSTITUT GUSTAVE ROUSSY, Villejuif (FR)

( * ) Notice: Subject to any disclaimer, the term of this patent is extended or adjusted under 35 U.S.C. 154(b) by 0 days.

(21) Appl. No.: 16/760,021

(22) PCT Filed: Oct. 31, 2018

(86) PCT No.: PCT/EP2018/079878
§ 371 (c)(1),
(2) Date: Apr. 28, 2020

(87) PCT Pub. No.: WO2019/086540
PCT Pub. Date: May 9, 2019

(65) Prior Publication Data
US 2020/0261513 A1   Aug. 20, 2020

(30) Foreign Application Priority Data
Oct. 31, 2017   (EP) .................................... 17306509

(51) Int. Cl.
*A61K 35/741*   (2015.01)
*A61K 39/00*    (2006.01)
(Continued)

(52) U.S. Cl.
CPC ........ *A61K 35/741* (2013.01); *A61K 39/4611* (2023.05); *A61K 39/4644* (2023.05);
(Continued)

(58) Field of Classification Search
CPC ....... G01N 2800/7028; G01N 33/5091; G01N 2800/52; G01N 2800/06; A61K 35/741;
(Continued)

(56) References Cited

U.S. PATENT DOCUMENTS

2017/0143775 A1* 5/2017 Mulder .................... A61P 37/00

FOREIGN PATENT DOCUMENTS

CA    3047029 A1 *  6/2018  ............. A61K 35/74
CN    103142656 A      6/2013
(Continued)

OTHER PUBLICATIONS

Reis et al., (Nutrition Research. vol. 37, Jan. 2017, pp. 1-19) (Year: 2017).*
(Continued)

*Primary Examiner* — Jana A Hines
(74) *Attorney, Agent, or Firm* — Arrigo, Lee, Guttman & Mouta-Bellum LLP

(57) ABSTRACT

The invention relates to the prognosis and treatment of colon cancer. In particular, the present invention concerns the role of intestinal microbiota in the anticancer immune response elicited by ileal enterocytes succumbing to apoptosis, and provides immunogenic compositions for treating colorectal cancer (CRC), as well as signatures for prognosing CRC evolution.

3 Claims, 20 Drawing Sheets

Figure 1G:
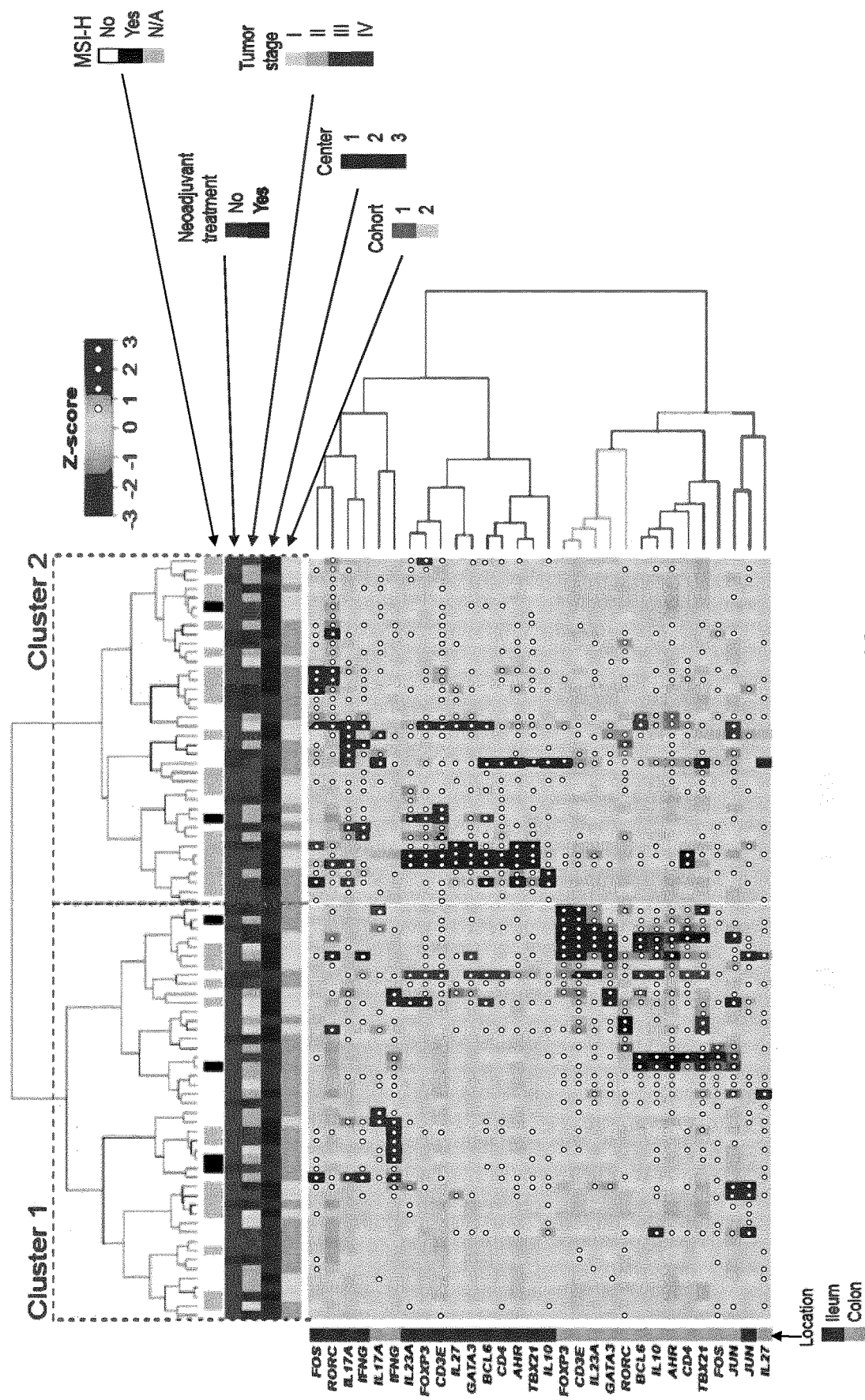

Specification includes a Sequence Listing.

(51) Int. Cl.
*C12N 1/20* (2006.01)
*G01N 33/50* (2006.01)

(52) U.S. Cl.
CPC ........... *C12N 1/20* (2013.01); *G01N 33/5091* (2013.01); *A61K 2239/50* (2023.05); *G01N 2800/06* (2013.01); *G01N 2800/52* (2013.01); *G01N 2800/7028* (2013.01)

(58) Field of Classification Search
CPC ...... A61K 35/12; A61K 31/282; A61K 35/74; A61K 35/17; A61K 35/38; C12Q 1/6886; A61P 35/00; C12N 1/20
See application file for complete search history.

(56) References Cited

FOREIGN PATENT DOCUMENTS

| EP | 2876167 A1 * | 5/2015 | ........... C12Q 1/6886 |
|---|---|---|---|
| RU | 2793582 C2 * | 4/2023 | ........... A61K 31/215 |
| WO | WO 90/01335 * | 2/1990 | ............. A61K 39/02 |
| WO | WO 2012142605 * | 10/2012 | ................ C12N 1/20 |
| WO | WO-2012142605 A1 * | 10/2012 | ................ C12N 1/20 |
| WO | 2014/182966 A1 | 11/2014 | |
| WO | WO-2016063263 A2 * | 4/2016 | ........... A61K 35/741 |
| WO | WO-2016086205 A2 * | 6/2016 | ......... A61K 31/7004 |
| WO | 2017/089794 A1 | 6/2017 | |

OTHER PUBLICATIONS

Capdevila et al., (Expert Rev Anticancer Ther. Aug. 2008;8(8)pp. 1223-1236 published Jan. 10, 2014) (Year: 2014).*

Wu Dang et al., Interleukin-17: A promoter in colorectal cancer progression, Clinical and Developmental Immunology vol. 2013, Article ID 436307, pp. 1-7, Dec. 7, 2013.

Jacouton Elsa et al., Probiotic Strain Lactobacillus casei BL23 Prevents Colitis-Associated Colorectal Cancer, Frontiers in Immunology, Nov. 2017, vol. 8, Article 155317, pp. 1-10.

International Search Report, PCT/EP2018/079878, Apr. 16, 2019.

Albert Abad Esteve: "Oxaliplatin, colorectal cancer and predictive factors", Clinical and Translational Oncology, Springer Milan, Milan, vol. 13, No. 6, Jun. 29, 2011 (Jun. 29, 2011), pp. 353-354, XP019921098.

Marie Vetizou et al: "Microbiote intestinal et reponses aux therapies anti-tumorales", M/S Medecine Sciences., vol. 32, No. 11, Nov. 1, 2016 (Nov. 1, 2016), pp. 974-982, XP055547456.

M. Vetizou et al: "Anticancer immunotherapy by CTLA-4 blockade relies on the gut microbiota", Science, vol. 350, No. 6264, Nov. 27, 2015 (Nov. 27, 2015), pp. 1079-1084, XP055310374.

Ericsson Aaron C et al: "Differential susceptibility to colorectal cancer due to naturally occurring gut microbiota.", Oncotarget Oct. 20, 2015, vol. 6, No. 32, Oct. 20, 2015 (Oct. 20, 2015), pp. 33689-33704, XP002779125.

Perspective Laurence Zitvogel: "Cancer and the gut microbiota: An unexpected link", Science Translation Medicine., vol. 21, No. 271, Jan. 20, 2015 (Jan. 20, 2015), pp. 271-1, XP055333413.

Azcarate-Peri L M Andrea et al: "The intestinal microbiota, gastrointestinal environment and colorectal cancer: a putative role for probiotics in prevention of colorectal cancer?" American Journal of Physiology. Gastrointestinal and Liver Physiology Sep. 2011, vol. 301, No. 3, Sep. 2011 (Sep. 2011), pp. G401-G424, XP002786398.

J. M. Pitt et al: "Fine-Tuning Cancer Immunotherapy: Optimizing the Gut Microbiome", Cancer Research, vol. 76, No. 16, Jul. 29, 2016 (Jul. 29, 2016), pp. 4602-4607, XP055522231.

* cited by examiner

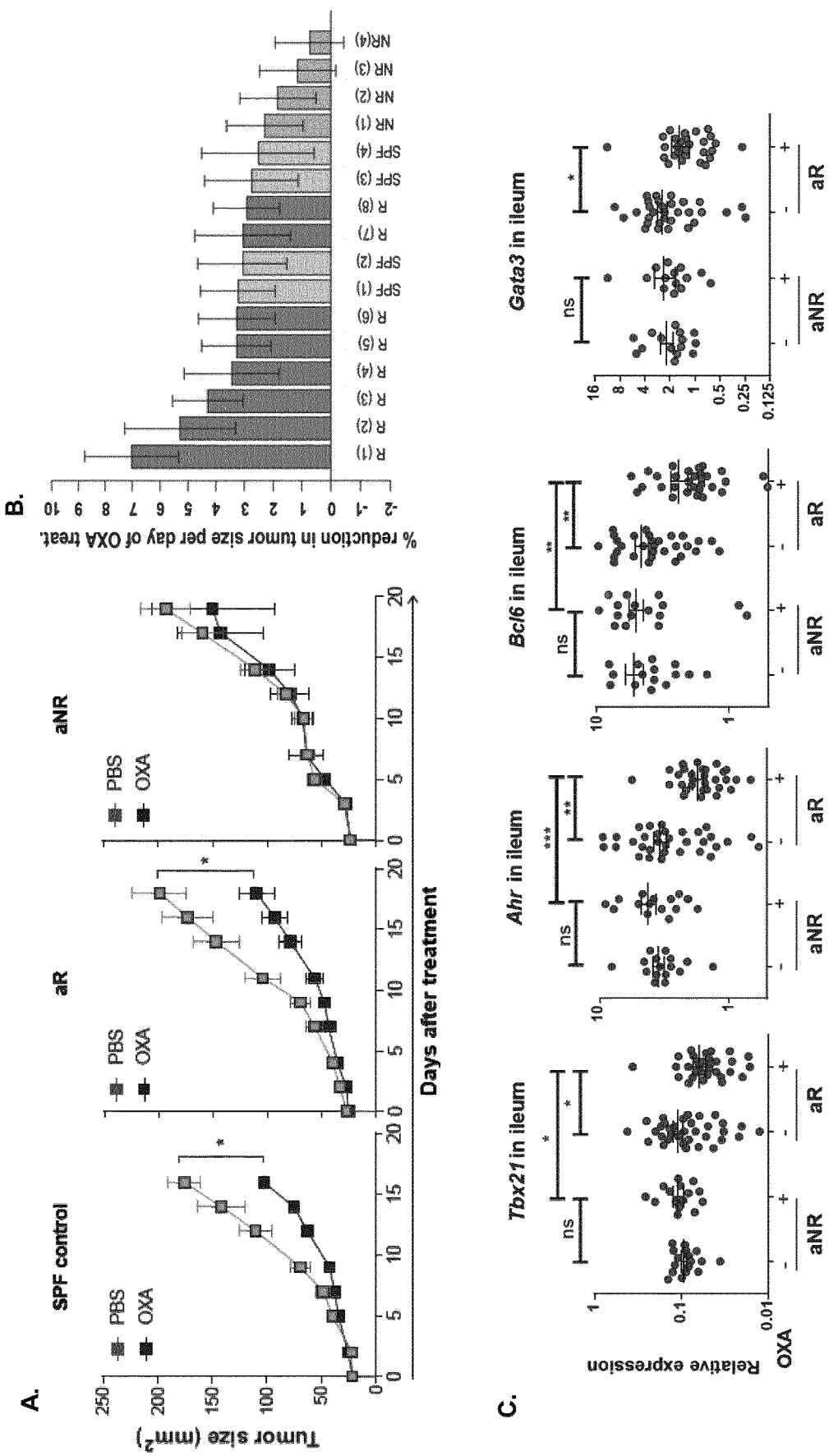
Figure 1A-C

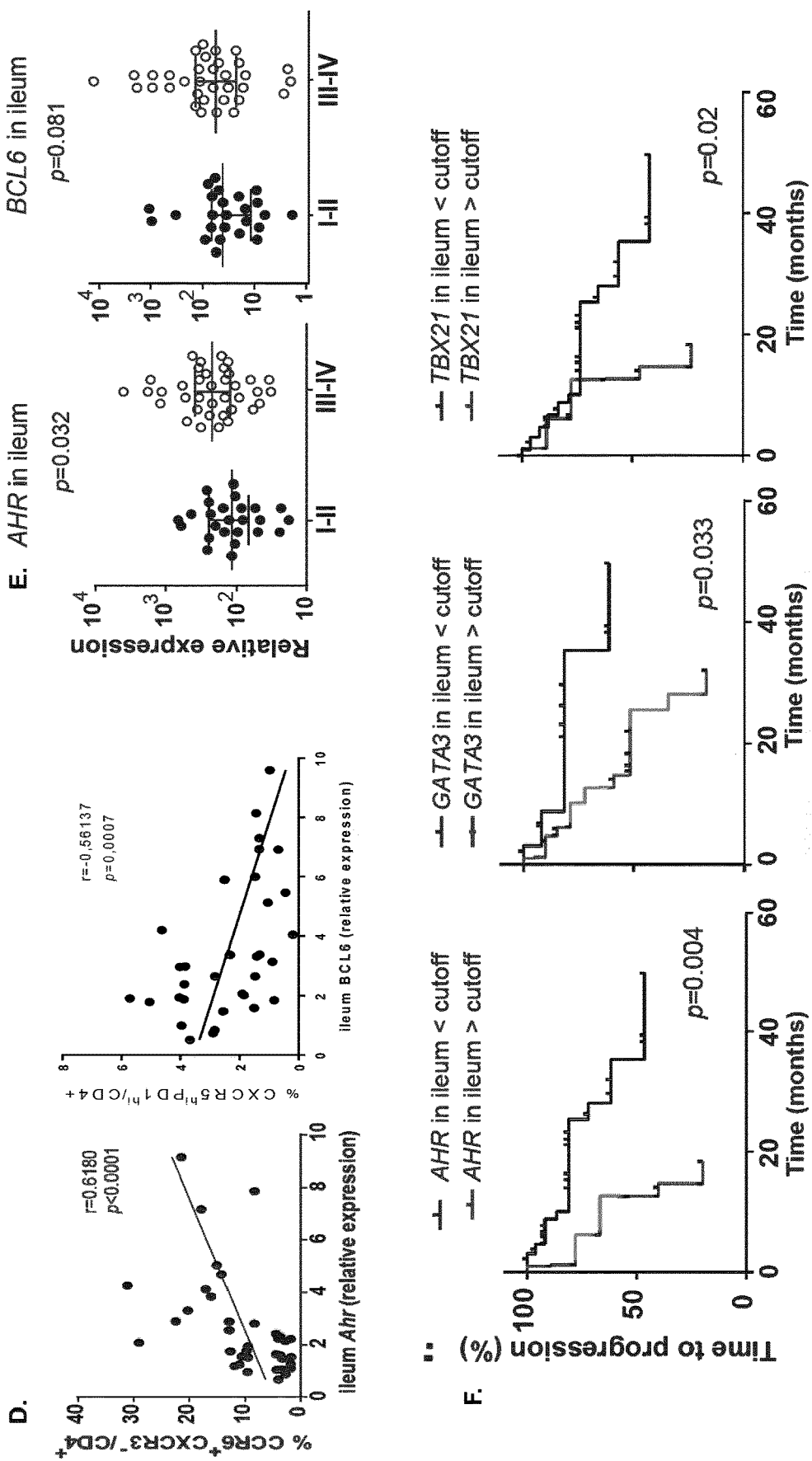
Figure 1D-F

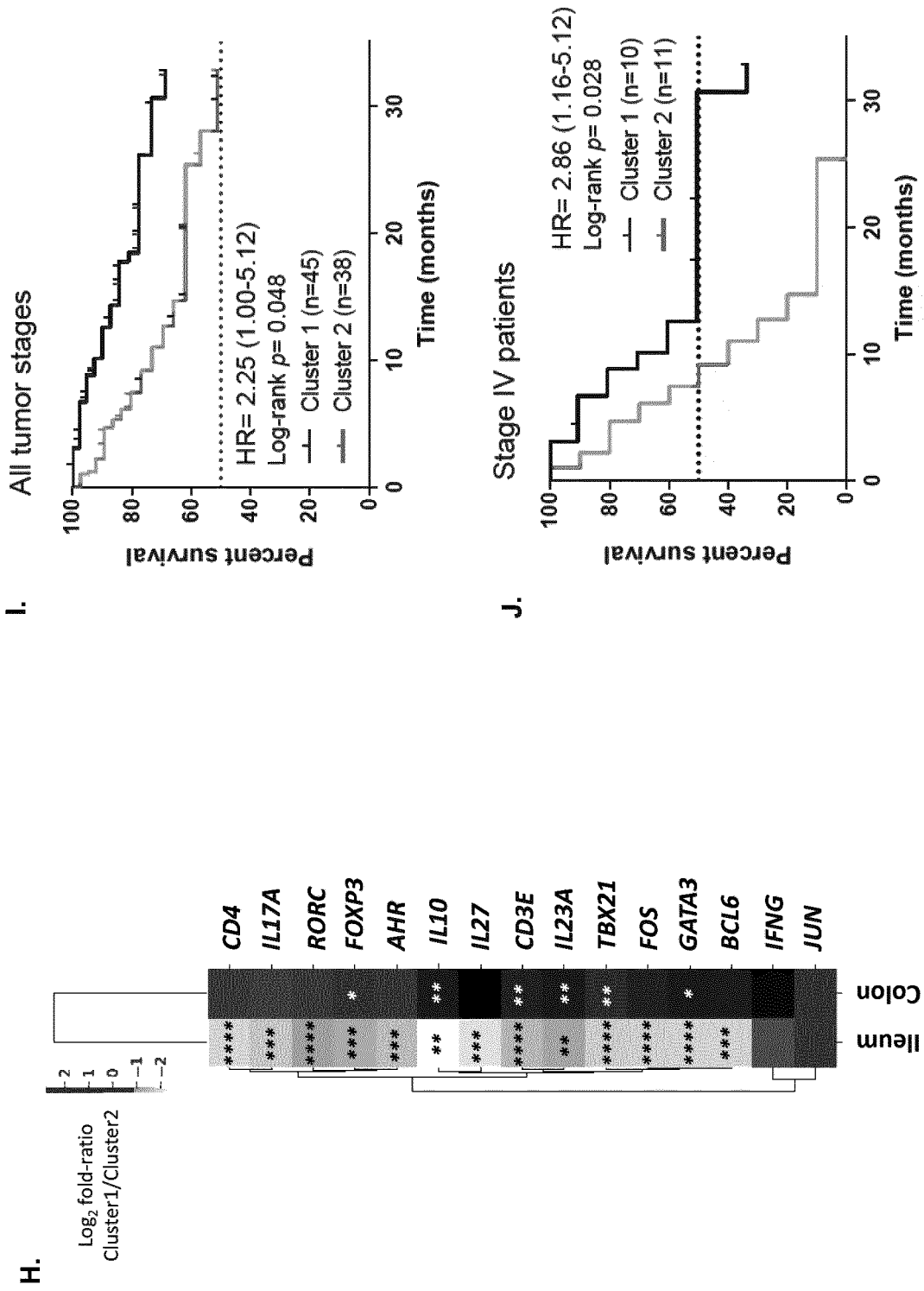
Figure 1H-J

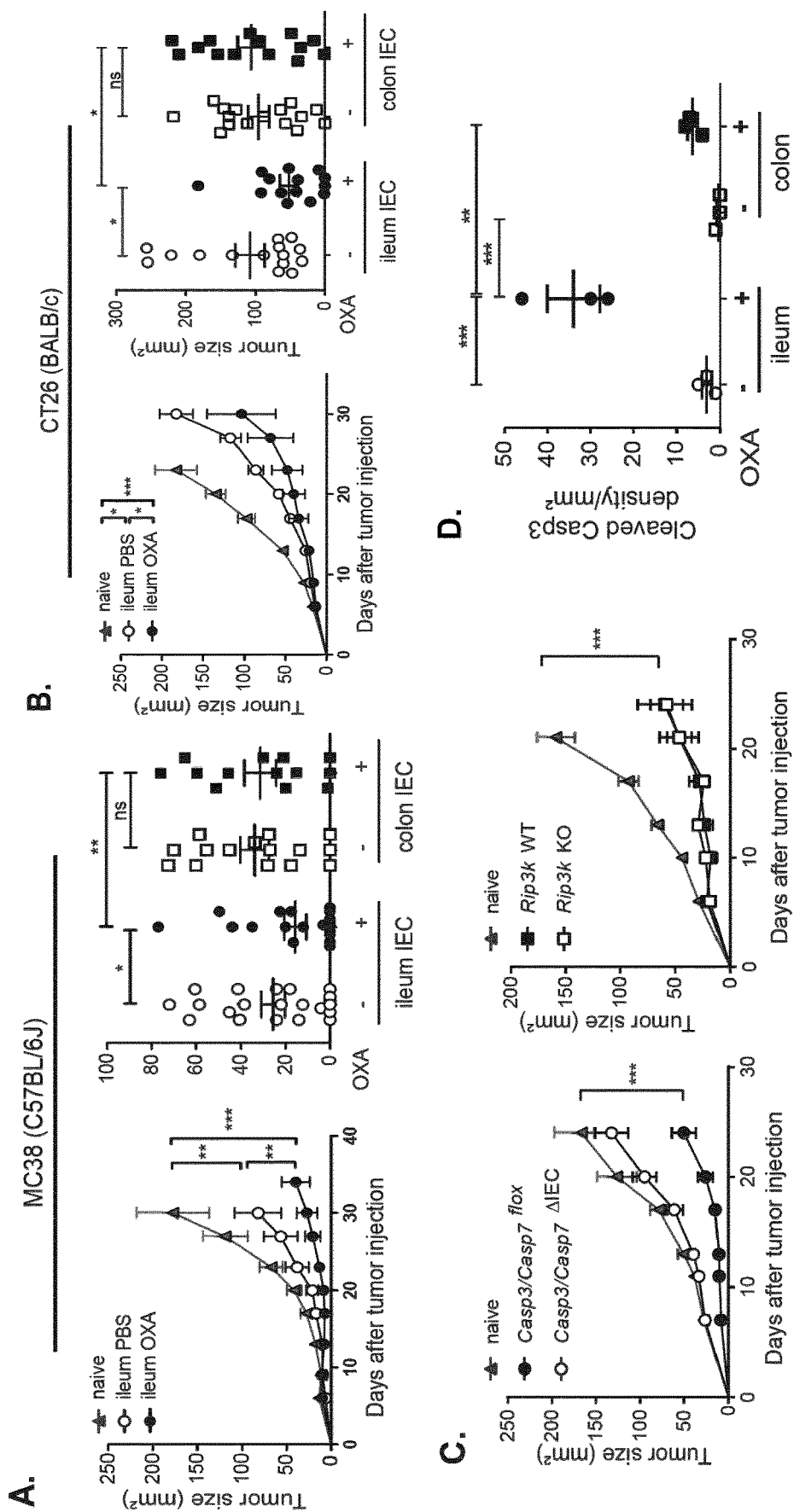
Figure 2A-D

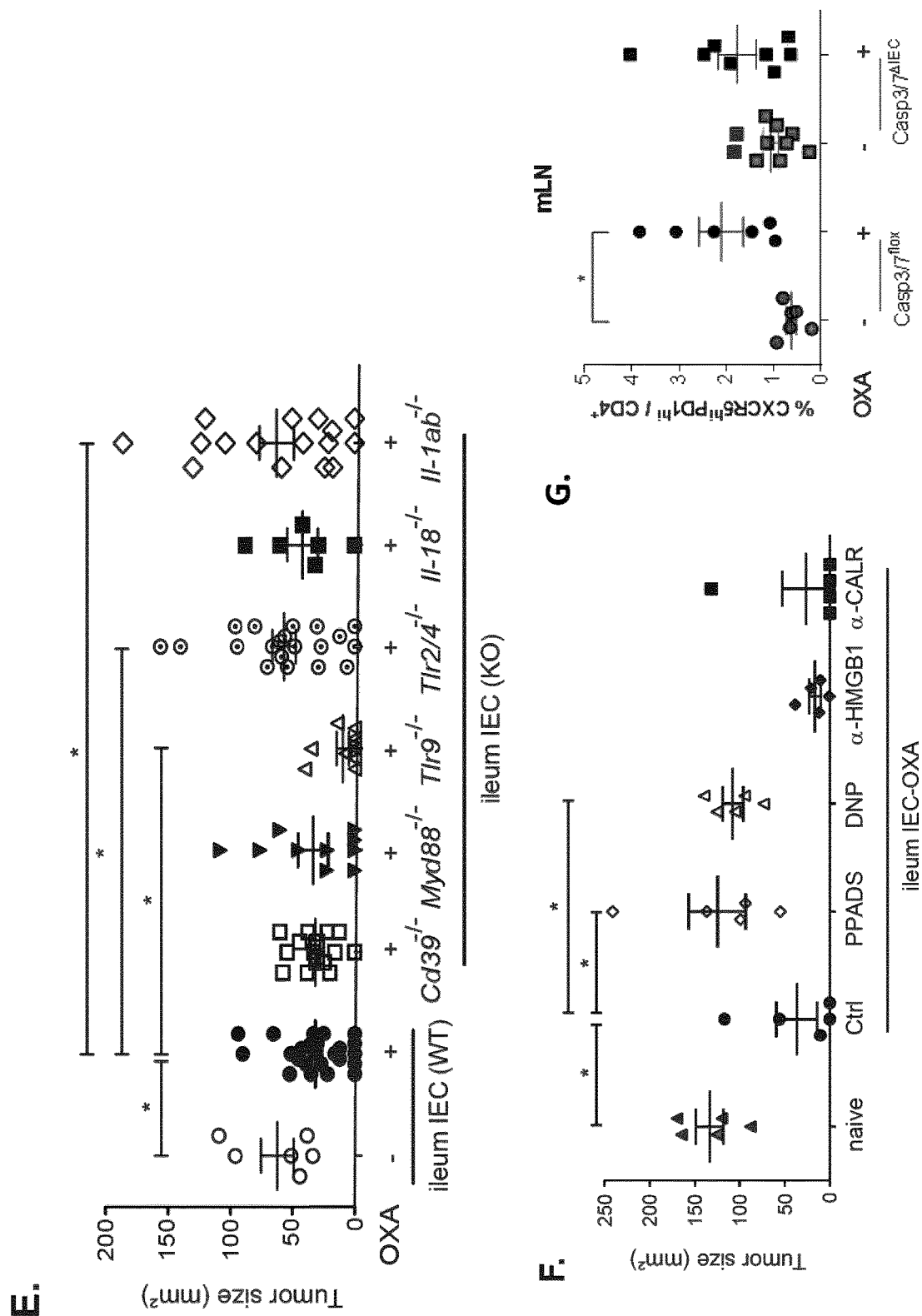
Figure 2E-G

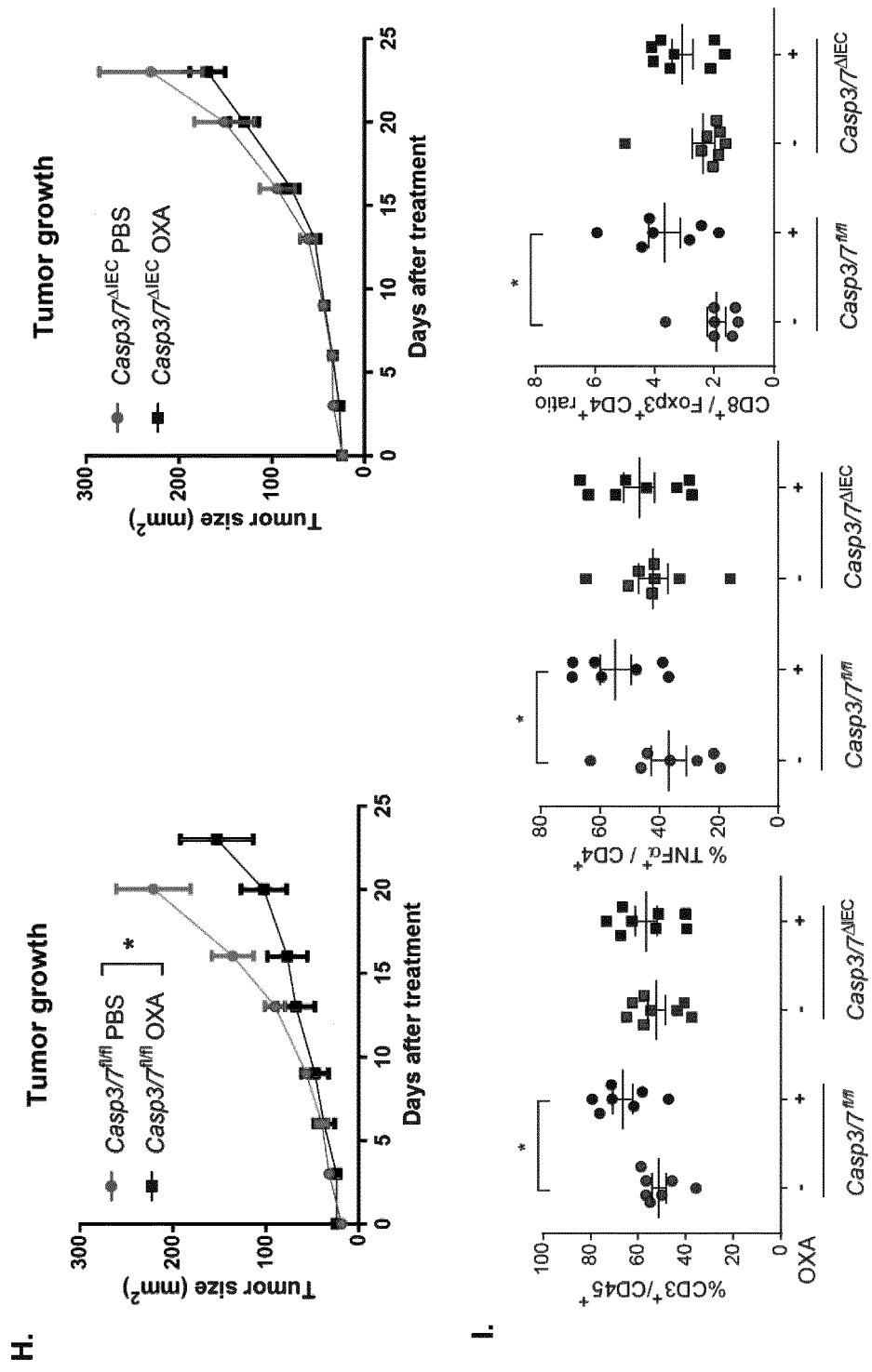
Figure 2H-I

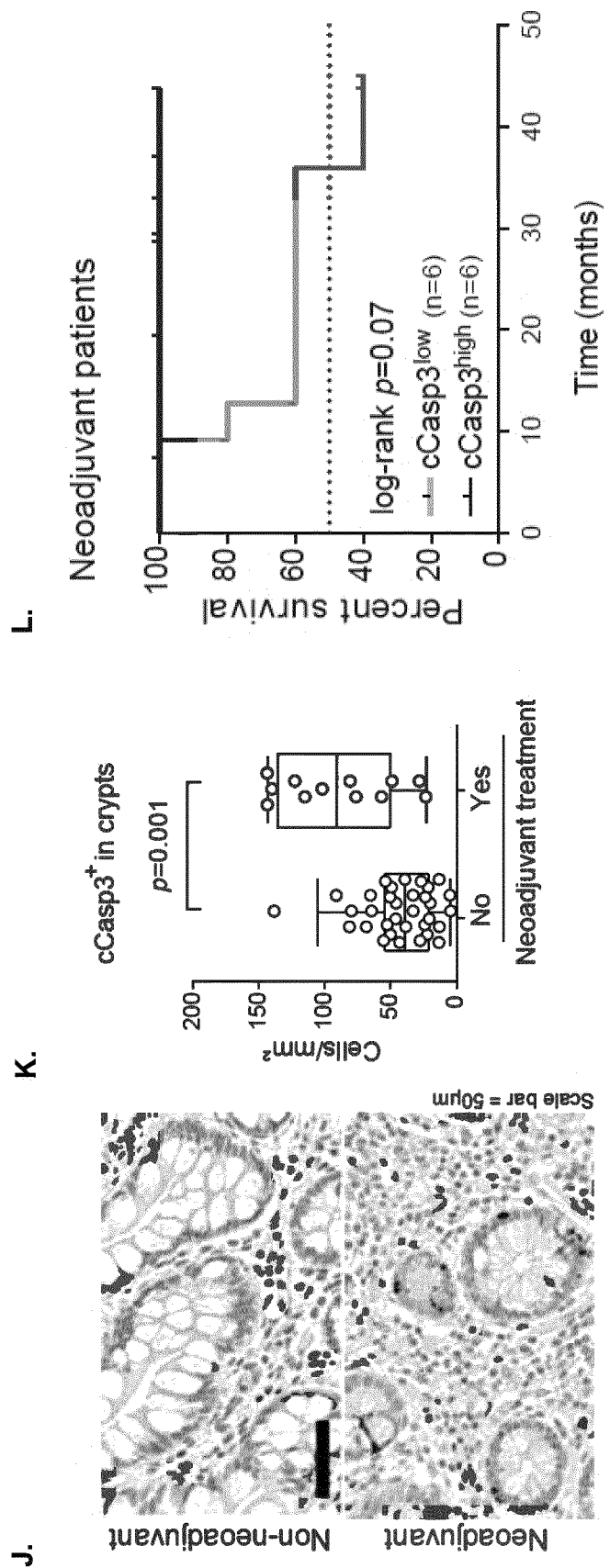
Figure 2J-L

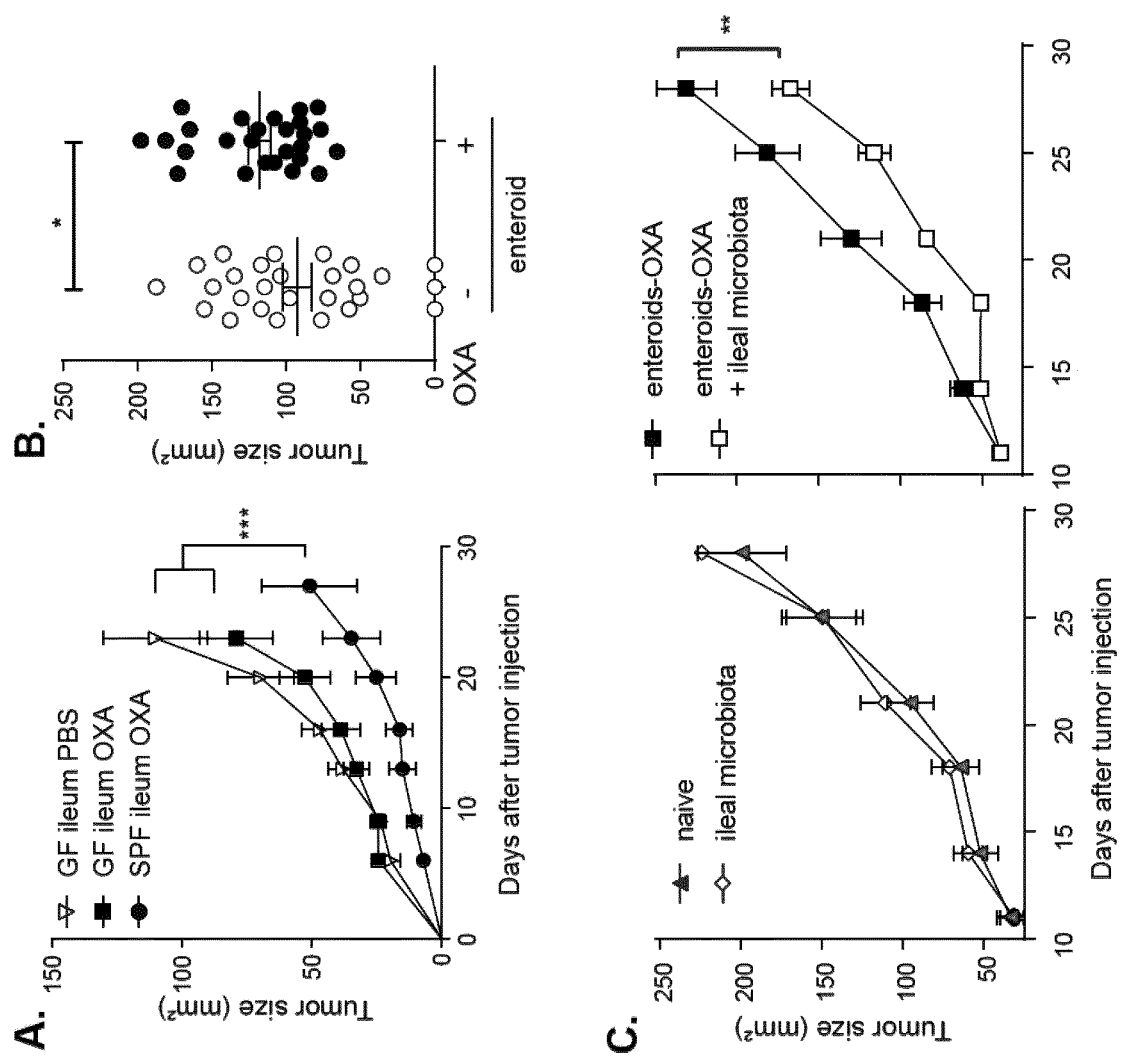
Figure 3A-C

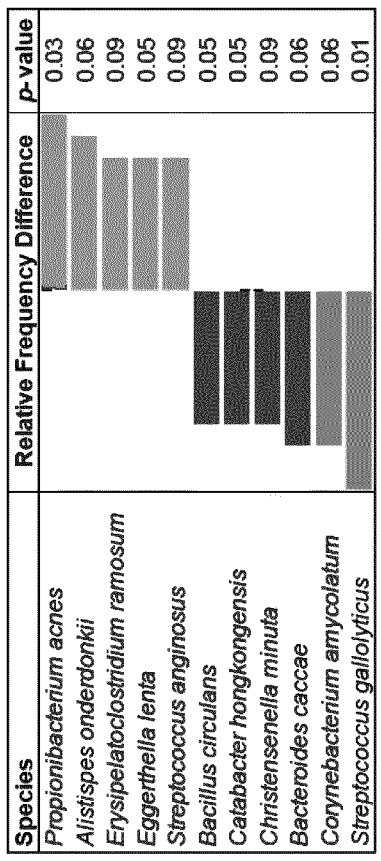
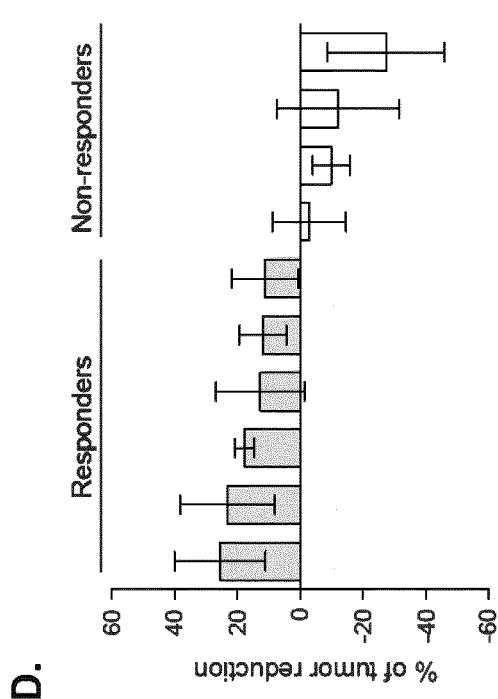
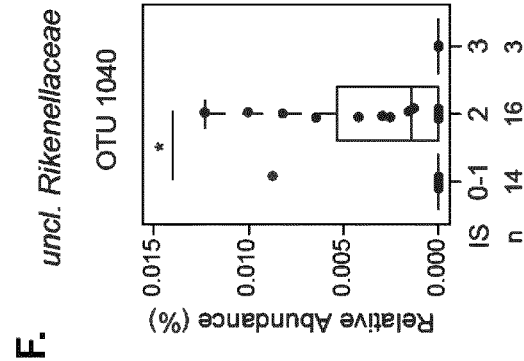
Figure 3D-F

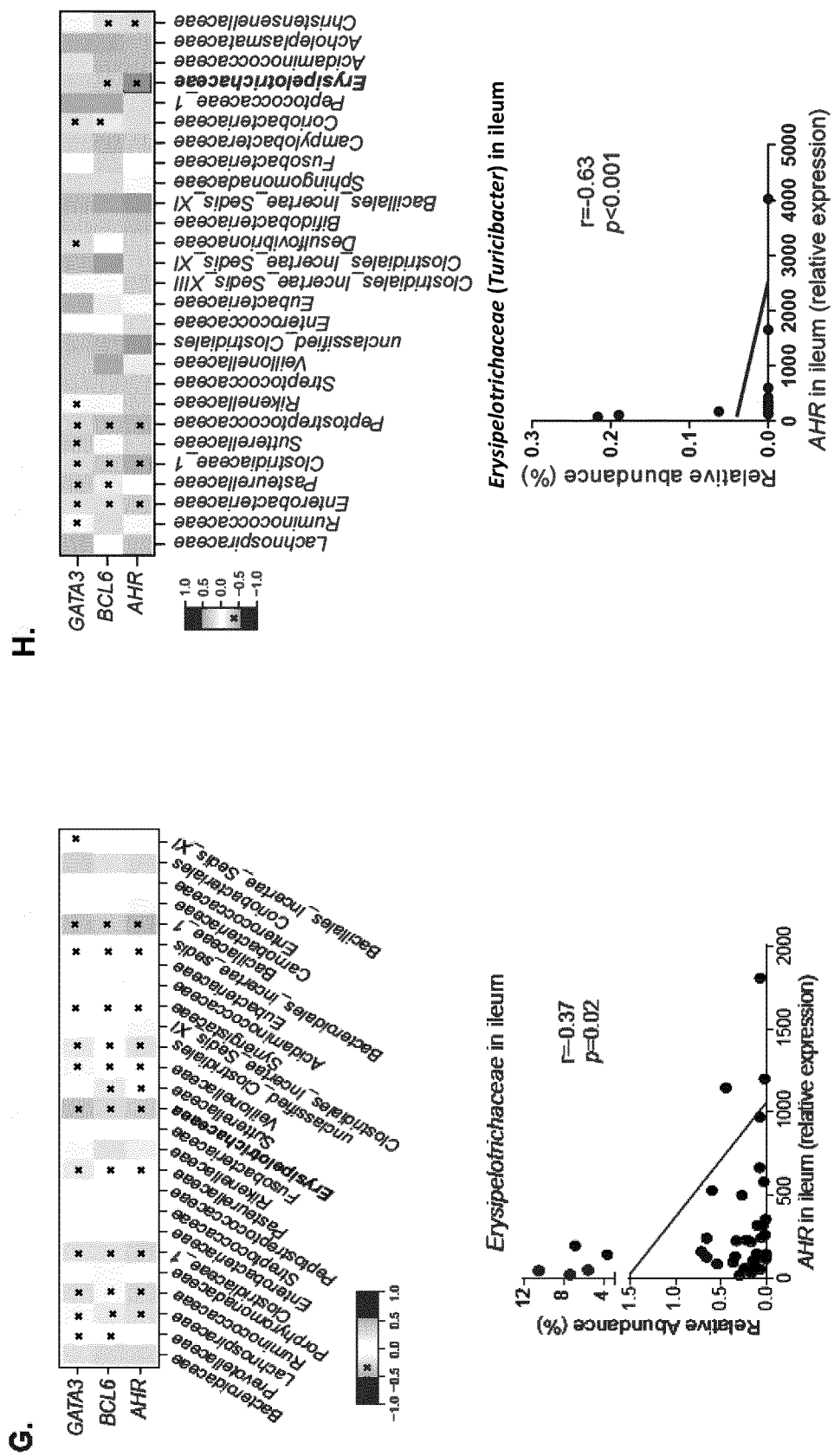
Figure 3G-H

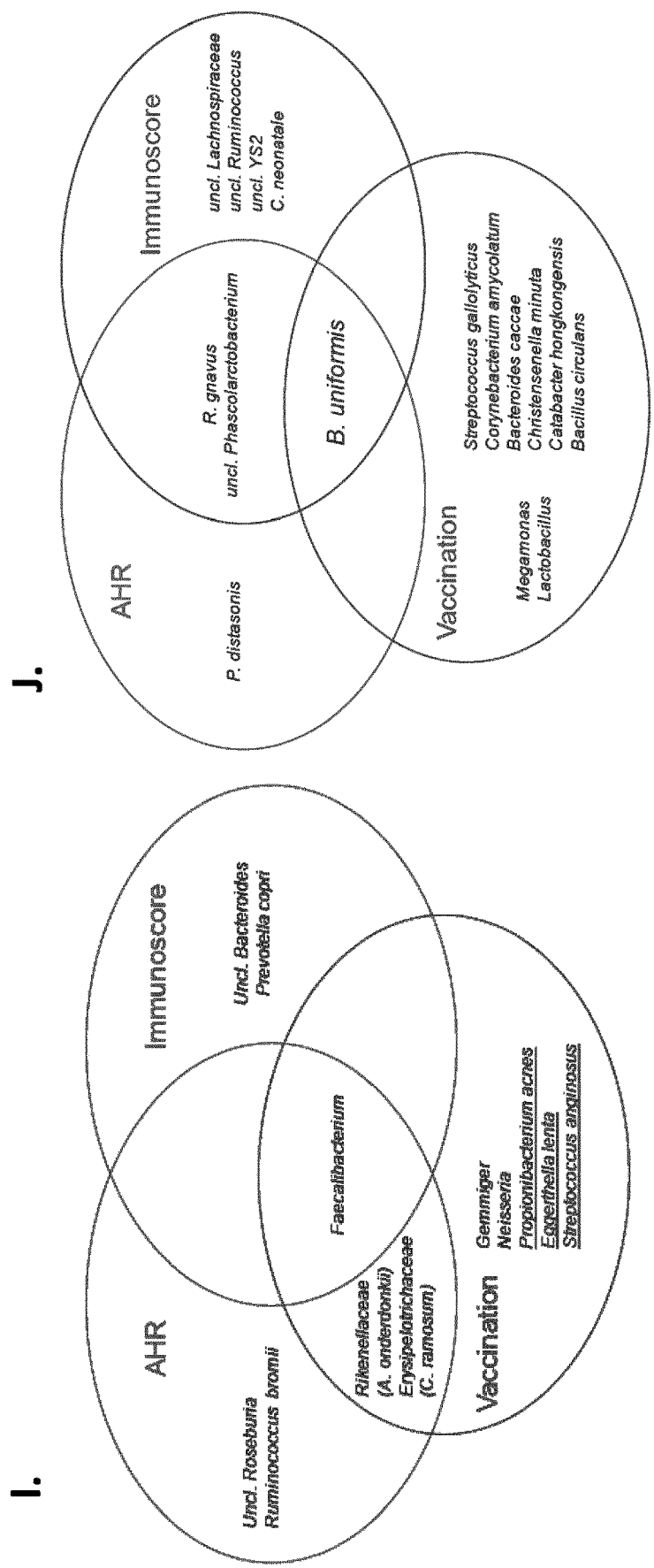
Figure 3I-J

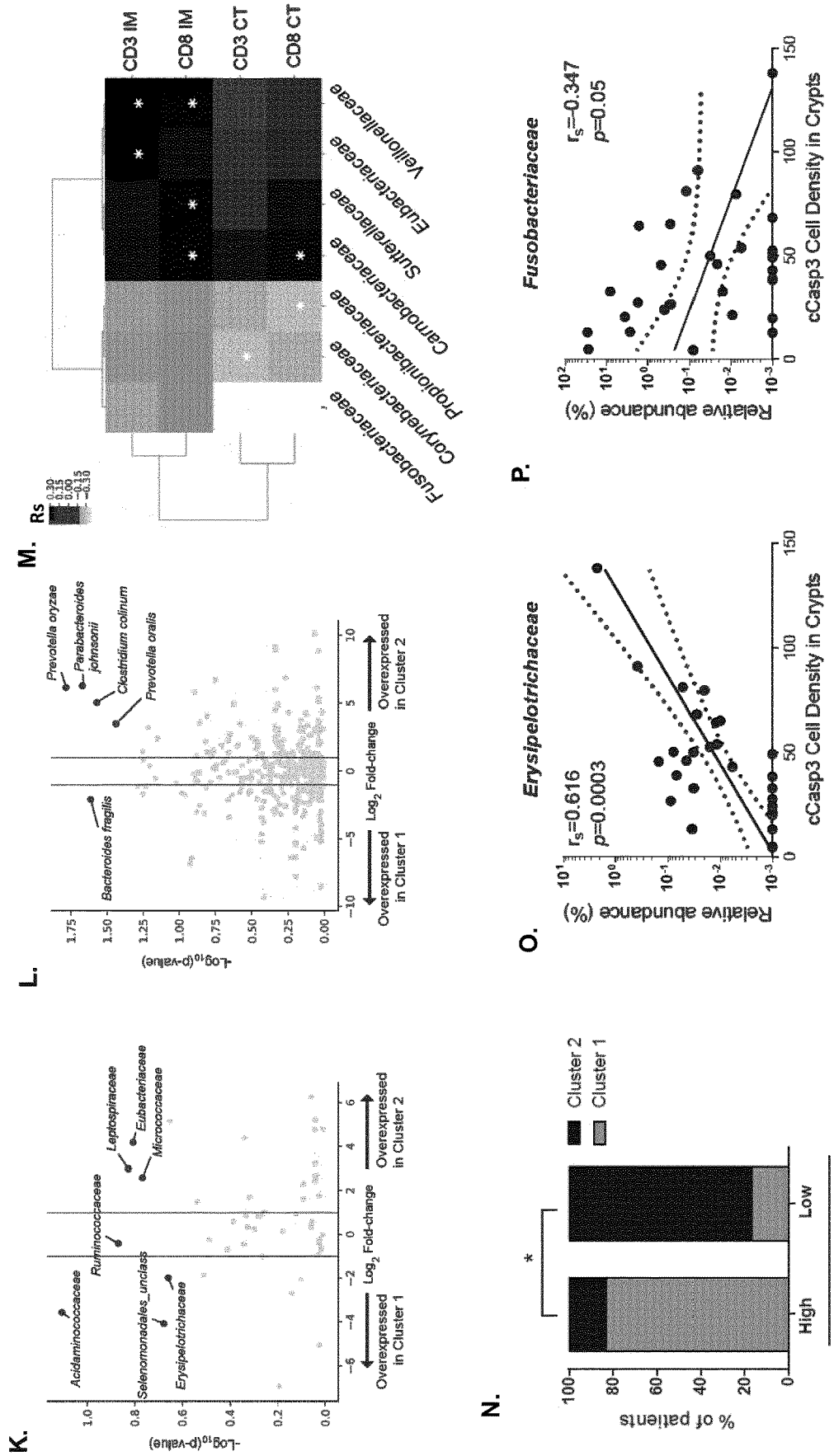
Figure 3K-P

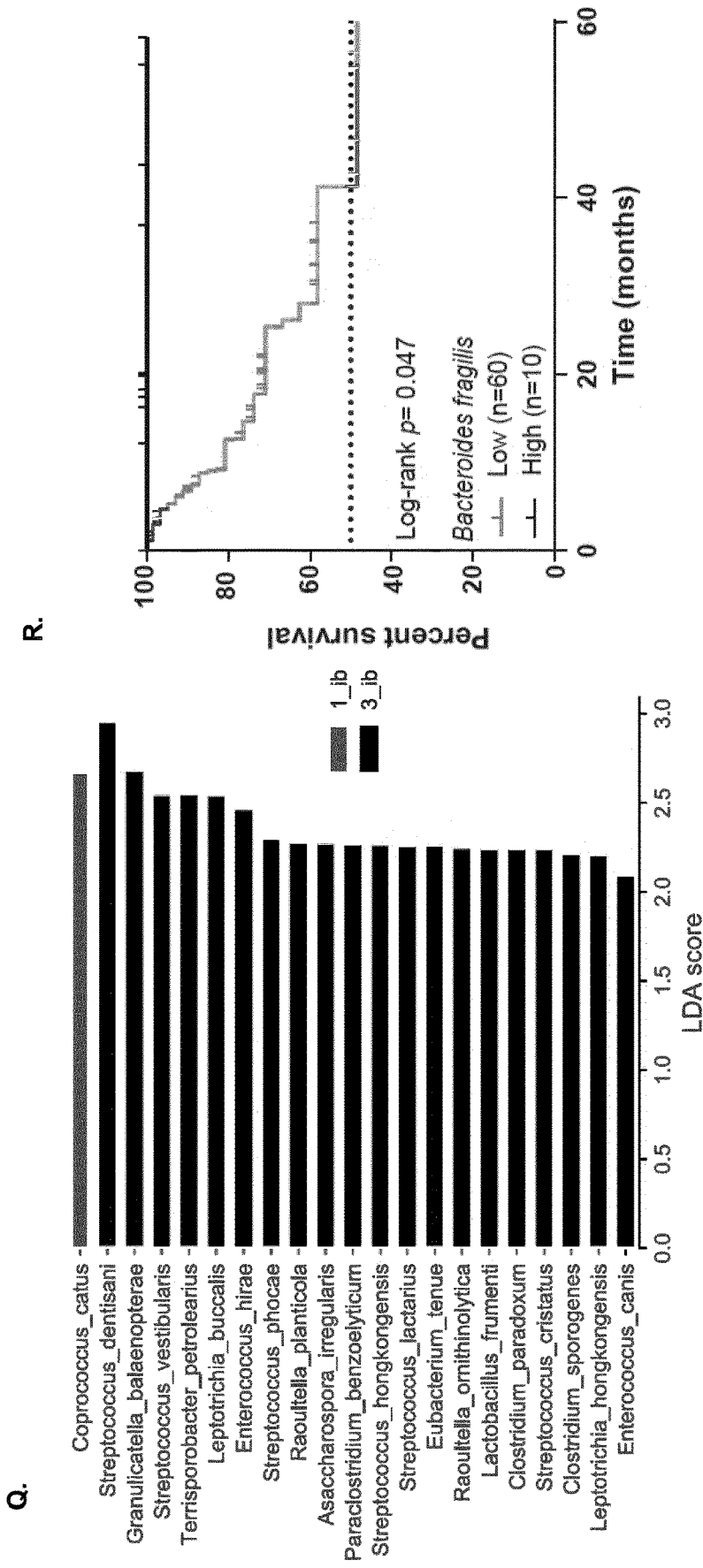
Figure 3Q-R

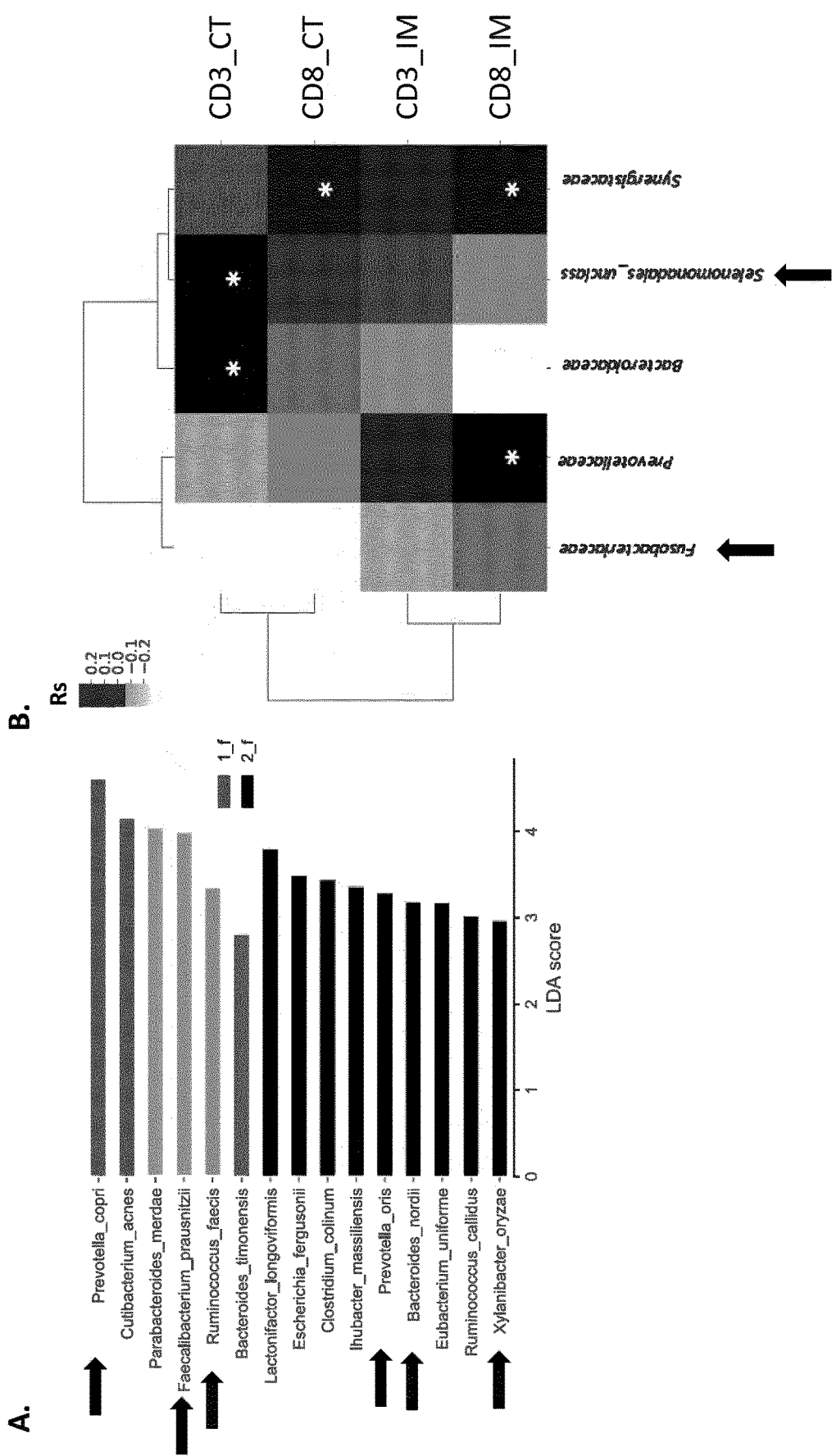
Figure 4A-B

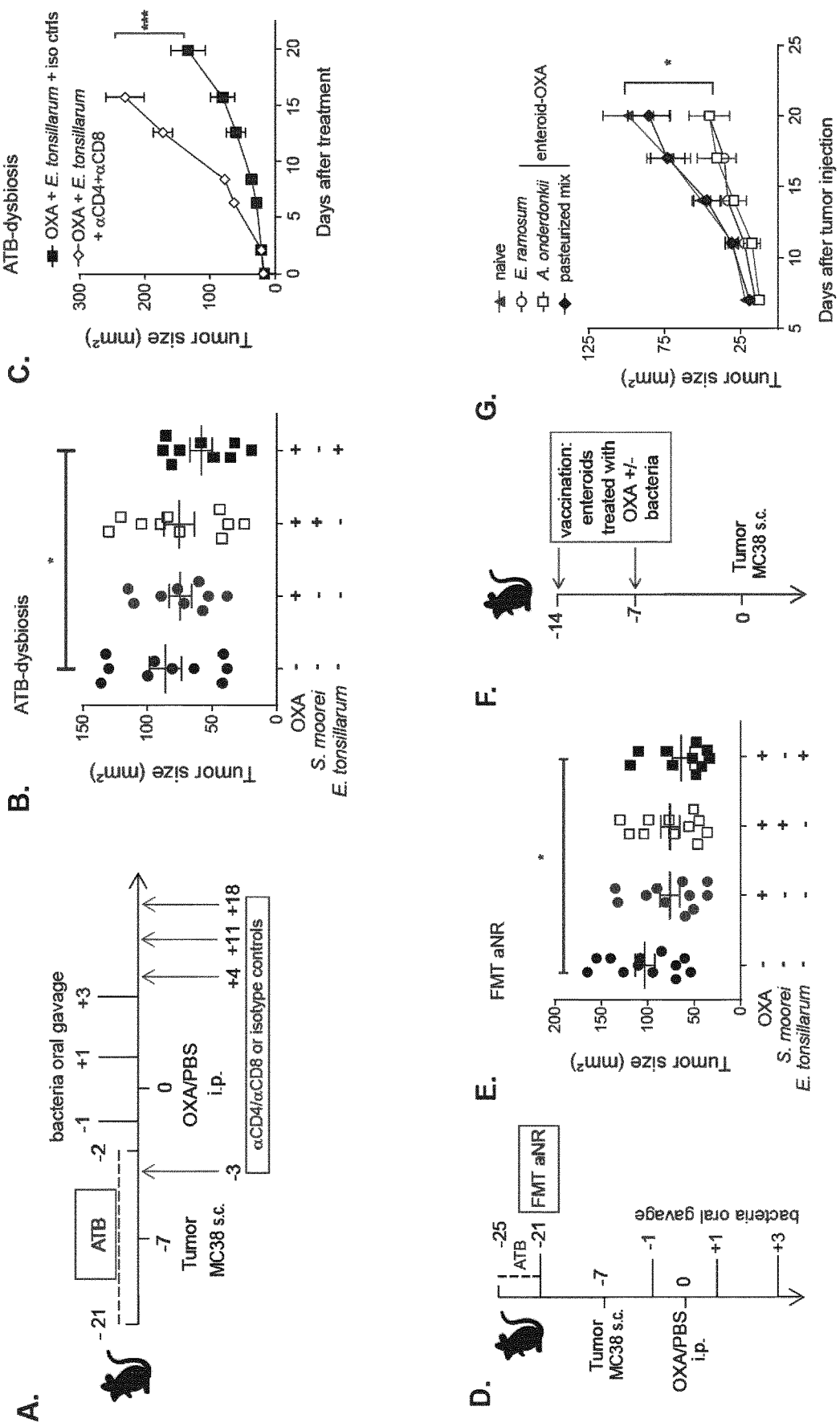
Figure 5A-G

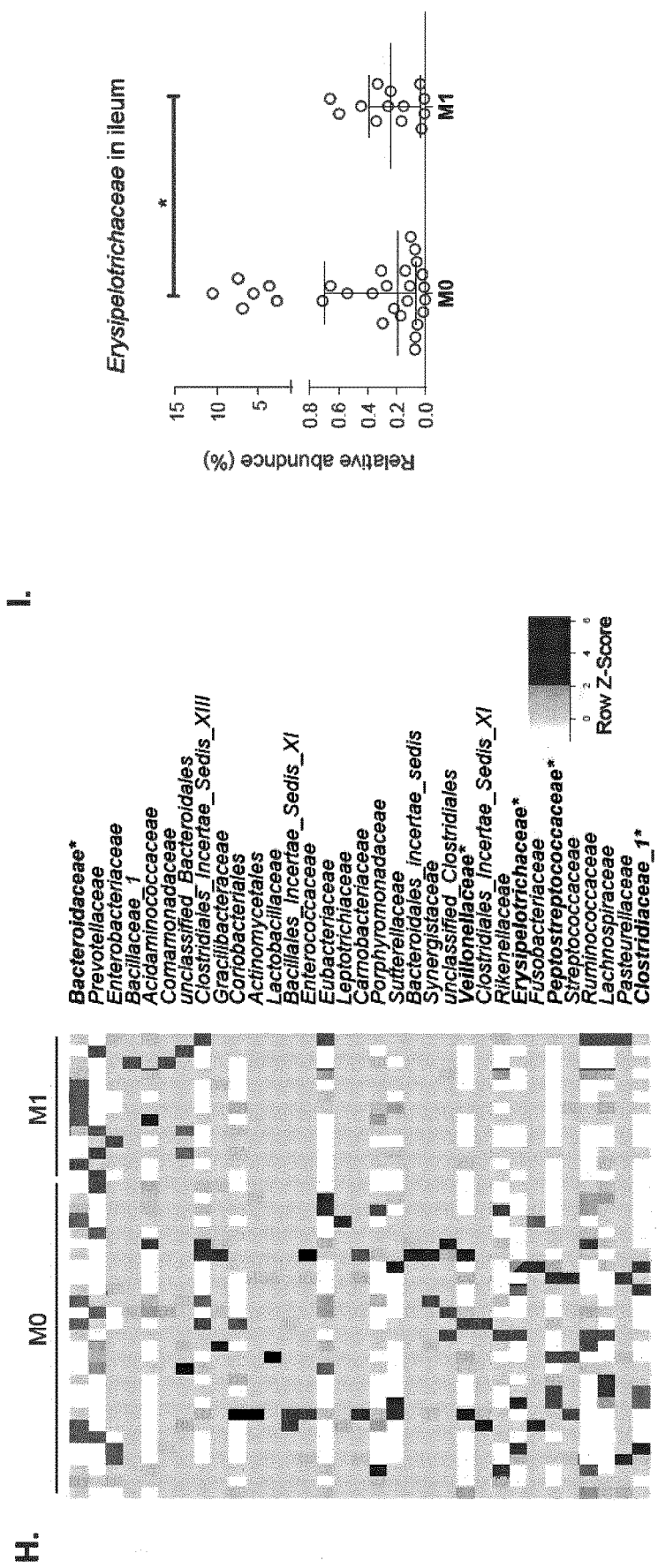
Figure 5H-I

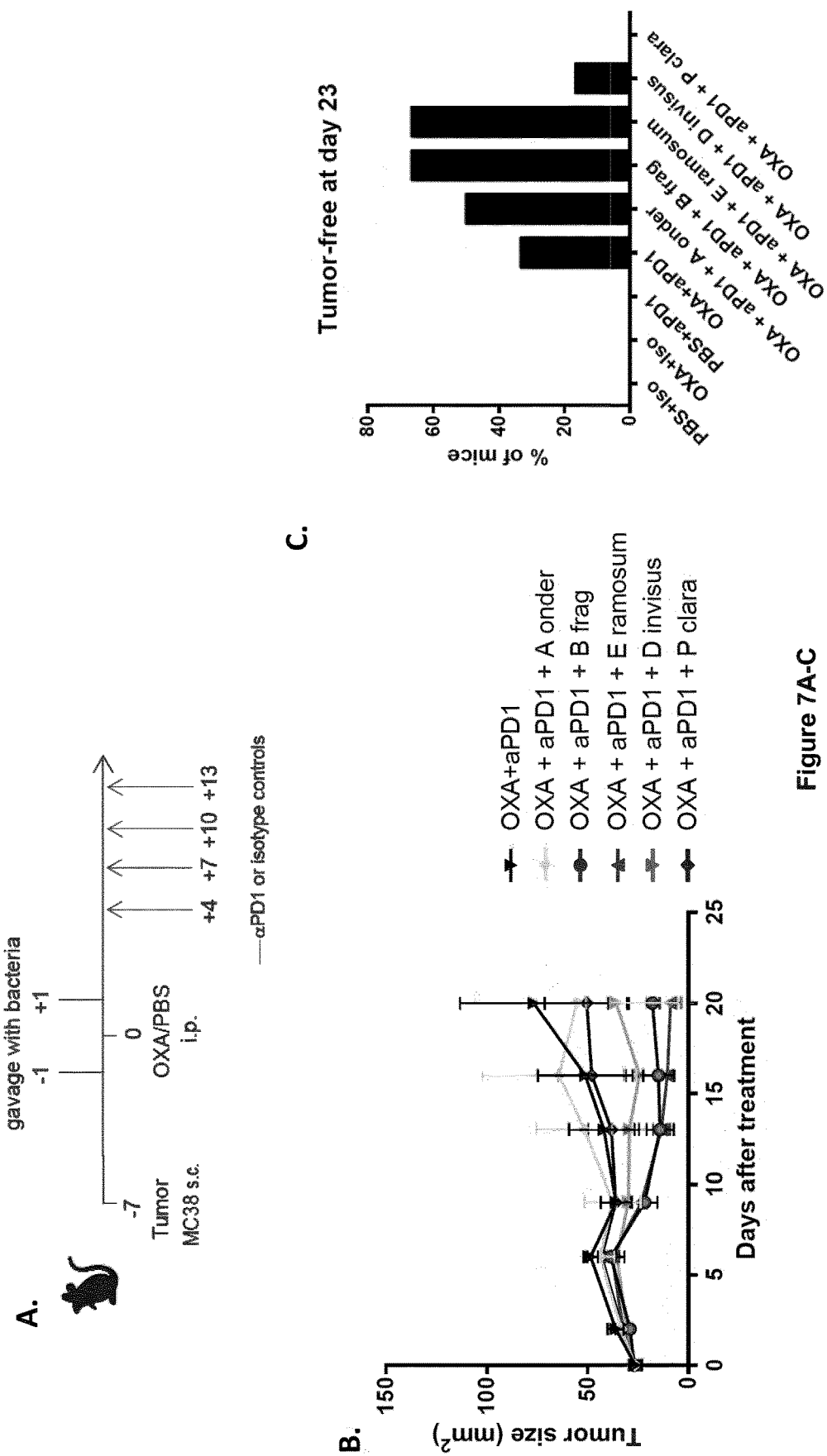
Figure 7A-C

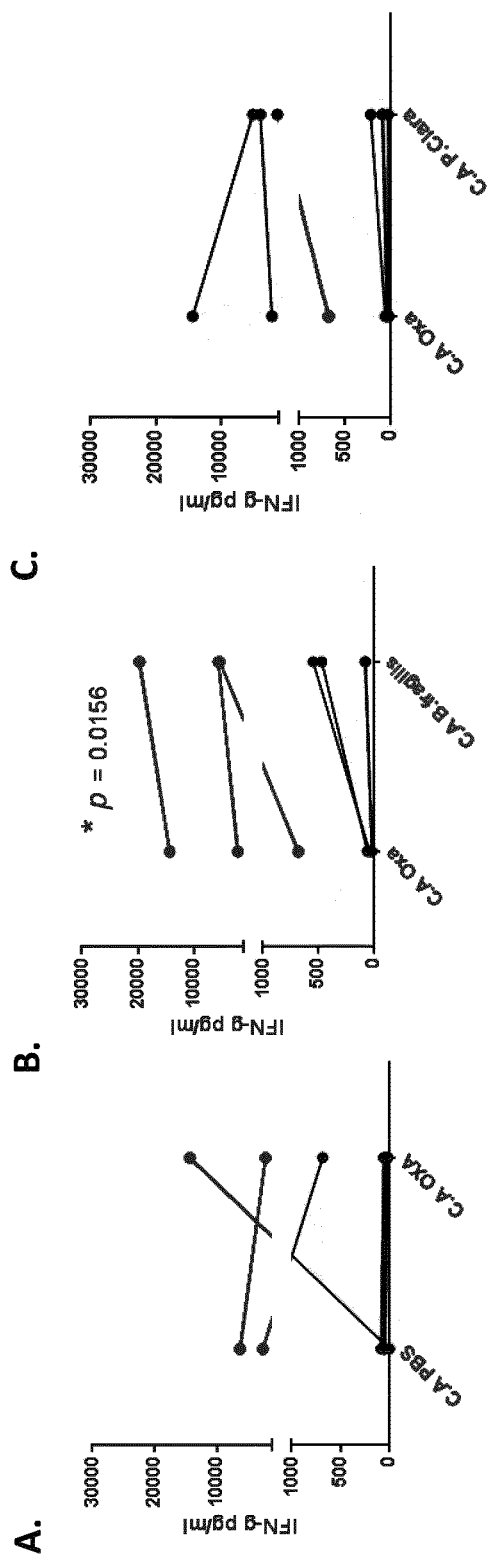
Figure 8A-C

BACTERIAL AND CELL COMPOSITIONS
FOR THE TREATMENT OF COLORECTAL
CANCER AND METHODS FOR ASSESSING
A PROGNOSIS FOR PATIENTS HAVING THE
SAME

FIELD OF THE INVENTION

The present invention relates to the prognosis and treatment of colon cancer. In particular, the present invention concerns the role of intestinal microbiota in the anticancer immune response elicited by ileal enterocytes succumbing to apoptosis, and provides immunogenic compositions for treating colorectal cancer (CRC), as well as signatures for prognosing CRC evolution.

BACKGROUND AND PRIOR ART

The intestinal mucosa is a dynamic interface between intestinal epithelial cells (IEC), local immunity and the microbial ecosystem (1). Sustained gut dysbiosis may be a risk factor for the exacerbation of colorectal inflammatory lesions leading to overt carcinogenesis (2, 3). Variations in the taxonomic footprints of microbial communities across major stages of the development of colorectal cancer (CRC) suggest a role for distinct communities of the gut ecosystem in carcinogenesis (4-6). CRC is the outcome of a multifactorial process arising from somatic molecular alterations influenced by diet, environmental and microbial exposure, as well as by host immunity (7). The abundance, functional competence and geodistribution of tumor-infiltrating T lymphocytes (TIL) within the tumor bed dictate the prognosis of CRC (8). Hence, a spontaneous or chemotherapy-induced adaptive immune response resulting in effector and memory Th1/Tc1 T lymphocyte activation suppresses tumor progression (9-11). CXCL13 and IL-21 are pivotal factors for the T follicular helper (TFH)/B cell axis correlating with survival (12). Oxaliplatin (OXA) is routinely used for CRC and induces immunogenic cell death (ICD) releasing damage-associated molecular patterns (DAMPs) (such as calreticulin, HMGB1, ATP, annexin A1, and CXCL10 (13-16)), thus inducing adaptive immune responses. The tumor, host, or environmental cues resulting in the accumulation of TIL in CRC remain to be elucidated. Previous studies have shown that lymphocyte infiltration is associated with microsatellite instability (MSI) resulting in the generation of truncated peptides produced by frameshift mutations (17-20). These neoantigens might predispose patients with MSI$^{high}$ CRC to responses with immune checkpoint inhibitors (21). However, the mechanisms accounting for the relative immunogenicity of the vast majority of MSI-negative CRC patients remain an open conundrum.

SUMMARY OF THE INVENTION

The inventors observed that broad spectrum antibiotics, which sterilize the intestine, reduced the efficacy of OXA against a colon cancer mouse model and prevented the release of anti-microbial peptides into feces, suggesting that OXA concomitantly affected both the gut and the tumor compartments. They thus decided to analyze whether the microbial composition of the intestine would influence the efficacy of OXA in treating CRC.

They found that the ileal microbiota determines the balance between tolerogenic versus immunogenic activity of dying intestinal epithelial cells. Anticancer immune responses protecting against colon cancer were associated with the ileal presence of Erysipelotrichaceae and Rikenellaceae. They also demonstrated that decreased ileal immune tone correlated with high levels of Erysipelotrichaceae, TFH activation in the mesenteric and tumor lymph nodes and prolonged progression-free survival in proximal colon cancer patients. These findings unveil novel associations between the intestinal microbiota, local immune responses and colon cancer treatment and prognosis, and form the basis for the present invention.

According to a first aspect, the present invention pertains to a composition comprising live bacteria selected from the group consisting of bacteria of the family Erysipelotrichaceae except those of the genus *Solobacterium*, bacteria of the family Rikenellaceae, bacteria of the class Negativicutes (in particular of the orders Selenomonadales and Acidaminococales), bacteria of the order Lactobacillales, bacteria of the species *Bacteroides fragilis* and mixtures thereof, for use in the treatment of colorectal cancer (CRC). These "immunogenic" bacteria/commensals can be administered as oral adjuvant in the treatment of CRC, in combination with immunogenic chemotherapy and/or immune checkpoint blockers.

According to another aspect, the invention pertains to a method of obtaining immunogenic enteroids useful for treating a CRC, comprising the steps of (i) incubating ileal enteroids with a composition comprising "immunogenic commensals" as above described (i.e., some Erysipelotrichaceae, Rikenellaceae, Negativicutes, Lacotacillales, *Bacteroides fragilis*), or any bacterium triggering ileal IL-1 beta transcription from enterocytes, and (ii) incubating these ileal enteroids with a cell death inducer.

An anticancer vaccine for treating a patient having a CRC or at risk of developing a CRC is also part of the present invention; such a vaccine comprises immunogenic enteroids obtained by the above method.

The present invention also relates to a method of obtaining T follicular helper cells and/or Th1 cells useful for treating CRC in a patient, comprising incubating autologous T helper cells with dendritic cells charged with autologous or allogeneic immunogenic enteroids obtained by the above method or with autologous or allogeneic primary intestinal epithelial cells exposed to the immunogenic commensals.

T follicular helper/Th1 cells obtained by this method are also part of the present invention, as well as their use for treating CRC, by adoptive transfer of said T follicular helper/Th1 cells in the patient.

According to another important aspect, the present invention pertains to a method for generating a prognostic and/or subtype signature for a patient with CRC, comprising:
   (i) in vitro assessing expression levels for one or more genes selected from the group consisting of CD3E, AHR, GATA3, TBX21, BCL6, CD4, RORC, FOXP3, FOS, JUN, IL17A, IL27, IL10, IL23A, and IFNG in a sample obtained from the terminal ileum mucosae of the patient, and
   (ii) comparing the expression levels in the patient with control expression levels.

The invention also pertains to a method for generating a prognostic and/or subtype signature for a patient with CRC, comprising:
   (i) in vitro assessing the presence of one or more "immunogenic" bacteria selected from the group consisting of Erysipelotrichaceae, Rikenellaceae, *Bacteroides fragilis, Prevotella copri, Faecalibacterium prausnitzii*, Negativicutes, Lactobacillales (in particular, *Enterococcus hirae*) and Selenomonadales in a sample obtained from the ileum mucosae of the patient or at least in a fecal sample from the patient, and (ii) in vitro assessing the presence of one or more "tolerogenic bacteria" selected from the group consisting of bacterial families Fusobacteriaceae, Bacteroidaceae (different from the afore mentioned *Bacteroides fragilis*), Tannerellaceae, Prevotellaceae, unclassified YS2, *Clostridium neonatale*, unclassified Lachnospiraceae, unclassified Ruminococcaceae, *Blautia*, *Christensenella minuta*, *Bacteroides caccae*, *Corynebacterium amycolatum*, *Streptococcus gallolyticus*, *Bacillus circulans*, *Ruminococcus gnavus*, uncl. *Phascolarctobacterium*, *Bacteroides uniformis* and *Catabacter hongkongensis*, wherein the presence of bacteria recited in (i) is indicative of a good prognosis and the presence of bacteria recited in (ii) is indicative of a bad prognosis.

Other methods for generating a prognostic and/or subtype signature for a patient with CRC are also provided, based on the ileal immune tone (determined by the number of cleaved Caspase 3 positive intestinal epithelial cells or the number of immune cells in ileal intestinal lamina propria and intraepithelial lymphocytes) or on the analyzis of *B. fragilis*-specific memory CD4+ Th1 response in a blood sample from the patient.

LEGENDS TO THE FIGURES

FIG. 1. Ileal immune tone correlates with prognosis of colon cancer in mice and patients.

A. Representative tumor growth curves for avatar responders (aR) and avatar non responders (aNR). Tumor size over time is represented as mean±SEM for natural tumor growth (PBS, grey) or after OXA treatment (black). Representative tumor growth of specific pathogen-free (SPF) controls is also shown. B. Graph contrasts OXA and PBS groups as % of decrease in tumor size per day of OXA treatment. aR, aNR, and SPF are represented with red, blue and grey bars, respectively. C. qRT-PCR of immune gene transcripts in ileal and colonic mucosae in PBS- and OXA-treated avatars at sacrifice (day 21). ANOVA $*p<0.05$, $p<0.01$, $*p<0.001$. D. Spearman correlations between ileal immune gene transcripts and percentages of TH17 and TFH determined by flow cytometry at sacrifice in tumor draining lymph nodes (tdLN) in OXA-treated avatar groups. E. Relative expression of AHR and BCL6 quantified by qRT-PCR. One dot represents one patient, median and interquartile ranges are depicted. Mann Whitney p-values are shown determining significant differences between stage I-II versus III-IV. F. Kaplan Meier time to progression (TTP) curves and Log-rank univariate analyses in 42 stage III-IV proximal colon adenocarcinoma (PCAC) patients (cohort 1 and 2 from initial analysis). Applying the median value of the cohort confirmed the results for AHR using the best cut-off value. G. Heatmap and dendrogram illustrating the agglomerative hierarchical clustering of PCC patients (expanded cohort n=83, columns) according to ileal and colonic immune gene transcription (rows) at surgery. Distance was measured with 1—Pearson correlation coefficient and agglomeration with Ward's method. Clinical variables and tissue of origin are indicted by color code on top and side border, respectively. H. Heat map showing the patterns of gene expression in ileum and colon as a Log 2 fold ratio between cluster 1 and cluster 2 individuals. Mann Whitney U test: $*p<0.05$; $p<0.01$; $*p<0.001$; $****p<0.0001$. I-J. Kaplan Meier curves for time to treatment failure (progression or cancer related death) segregated according to the clustering from panel G analyzed by Mantel Cox regression test in 83 PCC patients (I) or only in stage IV metastatic PCC patients (J).

FIG. 2. Protective role of intestinal caspases-3 and -7 in the immunogenic cell death of ileal enterocytes against colon cancer.

A-B. Vaccination of naïve C57BL/6J (A) or BALB/c (B) mice using ileal or colonic IEC which were or were not exposed to OXA to protect against syngeneic transplantable colon cancers, MC38 (A) or CT26, respectively (B). Tumor growth curves (left panels) showing one representative experiment and tumor size at day 21 of 2-3 pooled experiments (right panels). C. Vaccination experiment using WT littermates or genetic variants, Casp3/7$^{\Delta IEC}$ (left) or Ripk3$^{\Delta IEC}$ (right), as ileal IEC donors to immunize WT hosts. Tumor growth curves from a representative experiment are shown. D. Automatic quantification of positive immunohistochemical stainings of cleaved caspase-3 in colon and ileal mucosae after 6 h of OXA (or PBS) i.p. treatment. E-F. Vaccination experiments using WT or genetic variants (deficient in pattern recognition receptors [PRR] signalling pathways or DAMPs) as ileal IEC donors (E) or WT ileal IEC treated with neutralizing Abs or pharmacological inhibitors (F) to immunize WT hosts. Tumor sizes at day 21 of several independent experiments pooled are shown. G. Flow cytometry analyses of TFH cells among CD3$^+$CD4$^+$ of live cells in mesenteric lymph nodes (mLN) at sacrifice in tumor bearers treated with OXA i.p. (or PBS) in WT littermates or genetic variants of Casp3/7$^{\Delta IEC}$. One representative experiment is shown. ANOVA and t-test statistical analyses: $*p<0.05$, $p<0.01$, $*p<0.001$. H. Tumor growth kinetics of MC38 in a representative experiment in villin-driven caspase 3/7 gene deficient (Casp3/7ΔIEC) or caspase 3/7 floxed control littermates treated with OXA or PBS. Two-way ANOVA with specific Software (see Methods for details). I. Flow cytometric determination of various T cell subsets (CD3+, CD4+, CD8+, CD4+Foxp3+) in tumor beds at sacrifice in villin-driven caspase 3/7 gene deficient (Casp3/7ΔIEC) or caspase 3/7 floxed control littermates. One representative experiment is shown out of two yielding similar results. ANOVA and t-test statistical analyses: $*p<0.05$, $**p<0.01$. J. Representative micrograph pictures of immunohistochemistry for cleaved caspase 3 in PCC ileal specimens without or after neoadjuvant chemotherapy. Scale bars 50 µm. K. Statistical analysis of automated quantification of cleaved caspase 3+ cells using an algorithm to select crypts of 12 patients treated with neoadjuvant chemotherapy versus 33 untreated patients. Medians±5-95 percentile are depicted. Mann Whitney U test p-value is shown. L. Kaplan-Meier curves of overall survival in PPC patients who received neoadjuvant chemotherapy segregated according to the median value of ileal crypt cleaved caspase 3 (determined in K).

FIG. 3. The adjuvant role of ileal microbiota in the immunogenic cell death of ileal enterocytes against colon cancer.

A. Vaccination experiment using WT SPF or germ-free (GF) mice as ileal IEC donors to immunize WT hosts. Mean tumor growth curve of 1 representative experiment (6 mice/group) out of 3, yielding similar results. B. Vaccination experiment of naïve C57BL/6J mice using crypt stem cell-derived enteroids exposed to PBS or OXA to immunize against a lethal dose of MC38 cells. Tumor size at day 21 of 4 pooled experiments comprising 6-10 mice each. Each dot represents one mouse. C-D. Same experimental setting as in B but with the addition of ileal mucosal microbiota harvested from PCAC patients to vaccinate naïve hosts. Representative tumor growth curve in animals immunized with ileal mucosae-derived microflora alone (left) and OXA-IEC plus ileal mucosae-derived microflora (right) from the same patient (5 mice/group) (C). Results from 10 tested samples showing the % of reduction in tumor size between immunized versus non immunized mice at day 21 (D). E. Significant differences in enriched bacterial spp. between responders and non-responders by culturomic analysis of ileal microbiota from patients tested in D. F. Relative abundance of OTU1040 in ileal microbiome from PCAC patients according to their immunoscore (IS) in cohort 1. Student's t test, *p<0.05. G. Heat map of rho values for significant Spearman correlations (absolute rho>0.3) between bacterial families and expression levels of transcription factors in the ileum and correlation of the relative representation of Erysipelotrichaceae and ileal expression of AHR in cohort 1. H. Same setting as for cohort 1 depicted in FIG. 3G, but for cohort 2 (initial cohort 2 n=20): heat map of rho values for significant Spearman correlations (absolute rho>0.3) between bacterial families and expression levels of transcription factors in the ileum and representative dot plot for Erysipelotrichaceae associated with lower ileal expression of AHR in cohort 2. I. Venn diagram of common bacterial taxonomic ranks found in the three criteria associated with "immunogenic ileal apoptosis" in this study (immunoscore >2, AHR ileal expression levels below the median, immunizing properties in vivo [R]). J. Venn diagram of common bacterial taxonomic ranks found in the three criteria associated with non-"immunogenic ileal apoptosis" of this study (IS<2, AHR ileal expression levels above the median, non-immunizing properties in vivo [NR] in vaccinations experiments) as assessed using the 2 cohorts of patients. K-L. Volcano plots depicting the differential microbiota composition at family (K) and species (L) levels matching cluster 1 versus cluster 2 PCC patients as defined in FIG. 1G. Volcano plots were generated computing for each bacterial family (A) or species (B) residing in ileal mucosae of 83 (expanded cohort) PCC patients: i) the log 2 of fold ratio (FR) among the mean relative abundances in cluster 1 versus cluster 2 (x axis); ii) the co-log 10 of p-values deriving from Mann-Whitney U test calculated on relative abundances (y axis). Green dots are considered significant at p<0.05 (grey dots p>0.05). M. Heatmap showing Spearman correlation coefficients between ileal bacteria families and TIL composition defined by CD3+ and CD8+ T cells of the invasive margin (IM) or the core of the tumor (CT). Significant correlations (*p<0.05) are shown. N. The density of the cleaved apoptosis caspase 3 (cCasp3) is calculated at the bottom of the ileal crypt in neoadjuvant chemotherapy-treated PCC patients according to their segregation in cluster 1 or cluster 2 (FIG. 1G). The percentages of patients belonging to each cluster is indicated in conditions where cCasp3 is > or < to the cut-off value defined in FIG. 2K. O-P. Spearman correlations between cCasp3+ density in ileal crypts and bacteria families in the autologous ilea. Each dot represents one PCC patient. The continuous and dotted lines show the regression line and 95% of confidence intervals, respectively. Q. Linear discriminant analysis (LDA) coupled with the effect size measurements to represent ileal species differentially present among Immunoscore groups (1=poor prognosis; 3=good prognosis). LEfSeplots were generated with Python 2.7 and all species with LDA score ≥2 are shown. R. Kaplan Meier curves for time to treatment failure (progression or cancer related death) segregated according to the relative abundance of *Bacteroides fragilis* in ileal mucosae at surgery in 70 PCC patients, analyzed using the Mantel Cox regression analysis and at best cutoff value using Cutoff Finder method.

FIG. 4. Fecal microbiota signatures correlate with ileal microbial signatures.

A. Linear discriminant analysis (LDA) coupled with the effect size measurements to represent fecal species differentially present among Cluster 1 and Cluster 2. LEfSeplots were generated with Python 2.7 and all species with LDA score ≥2 are shown. Commonalities with ileal species are indicated with an arrow. B. Heatmap showing Spearman correlation coefficients between fecal bacteria families and TIL composition defined by CD3+ and CD8+ T cells of the invasive margin (IM) or the core of the tumor (CT). Significant correlations (*p<0.05) are shown. Commonalities with ileal families are indicated with an arrow.

FIG. 5. Compensatory effects of *Alistipes* sp. and Erysipelotrichaceae restoring oxaliplatin anticancer efficacy in conditions of gut dysbiosis.

A-C. ATB-treated SPF mice injected with MC38 and treated with oral gavages of $10^9$ cfu of live *Erysipelothrix tonsillarum* or *Solobacterium moorei* 1 day before and after OXA ip treatment (A), in the absence (B) or presence of depleting anti-CD4$^+$ and anti-CD8$^+$ Abs (C). Tumor size at day 21 (pool of two experiments) (B) and tumor growth (of one representative experiment) (C). D-E. Bacterial compensation performed in aNR. ANOVA statistics: *p<0.05. F-G. Immunization of naïve mice using enteroids (same setting as in 3A) whereby OXA-treated enteroids have been concomitantly exposed to live (or pasteurized) bacteria and then neutralized by ATB prior to s.c. immunization. The graph depicts tumor growth (of one experiment) (G). H. Heat map of main bacterial families according to metastases occurrence at diagnosis in cohort 1. Significant families are labeled (*), Student's t-test. I. Relative abundance of Erysipelotrichaceae in ileal content in PCAC patients with or without metastases. *p<0.05 Student's t-test.

Figure 6:
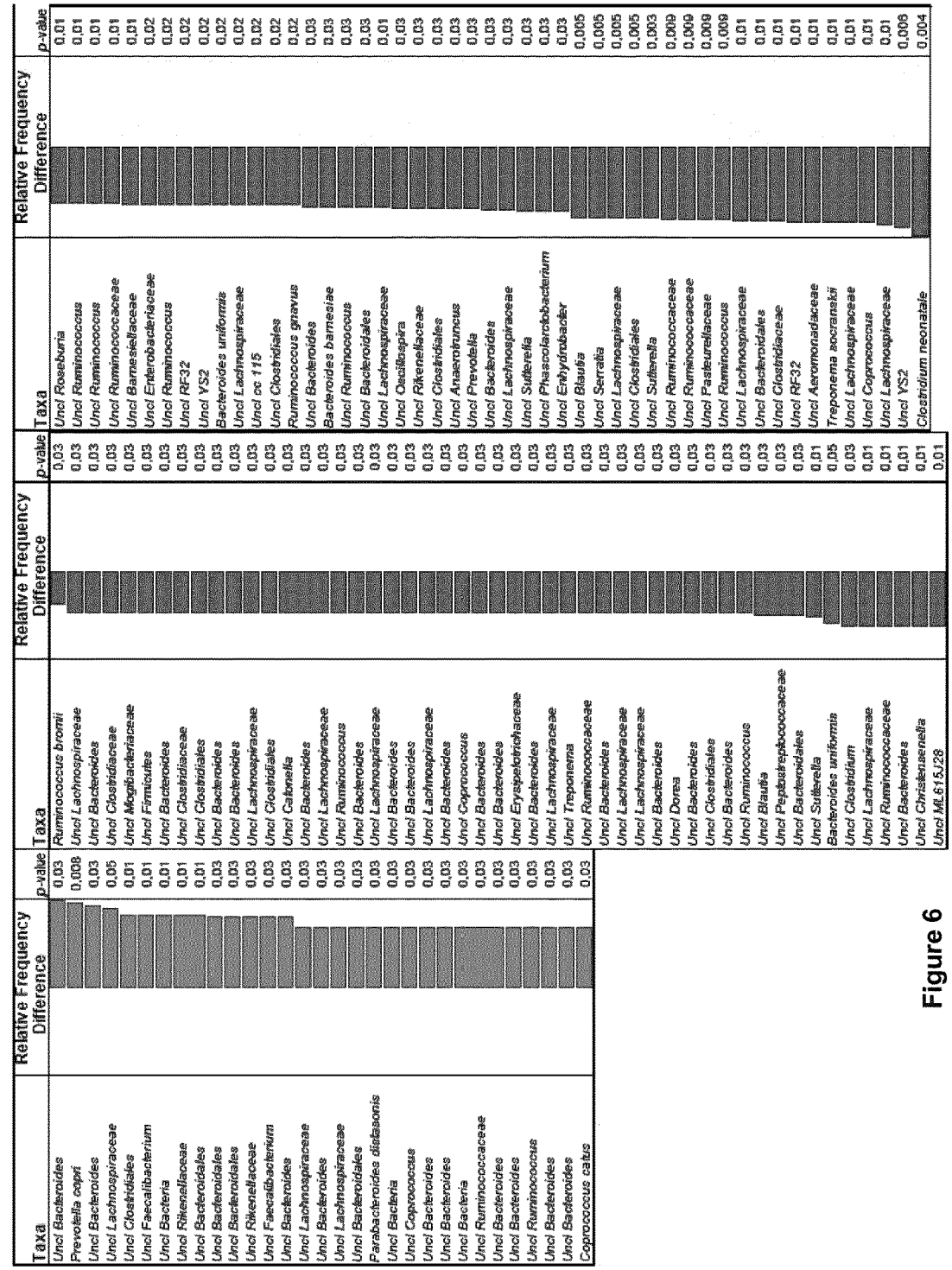

FIG. 6. Ileal microbiome according to cancer immunoscore in PCAC patients (cohort 1).

Significant differences in enriched bacterial spp. in ileal mucosae from patients harboring tumors with high immunoscore (IS 2-4) versus low immunoscore (IS 0-1) by MiSeq 16S rRNA gene analysis of ileal microbiota. Data from cohort 1. Chi-square test p-values are shown.

FIG. 7. Immunogenic effects of *B. fragilis* and bacteria belonging to Erysipelotrichaceae improving anticancer efficacy of the combinatorial regimen composed of oxaliplatin and anti-PD-1 antibodies.

A. Experimental setting: SPF mice injected with sc MC38 and treated with oral gavages of $10^9$ cfu of live bacteria (listed in the graph: *A. onder*: *Alistipes onderdonkii*, *B. frag*: *Bacteroides fragilis*, *C. ramosum*: *Erysipelatoclostridium ramosum*, *D. invisus*: *Dialister invisus*, *P. clara*: *Prevotella clara*) 1 day before and after OXA ip treatment in combination with anti-PD-1 Abs. B. Tumor growth curves represented as means+/−SEM of tumor sizes overtime, 6 mice/group, one representative experiment is depicted. Anova stats: *p<0.05, **p<0.01. C. Percentages of tumor free mice at the end of the experiment (one representative experiment is depicted).

FIG. 8. Differentiation of CD4 naïve T cells into Th1 cells using dendritic cells exposed to HIEC treated with immunogenic bacteria and the cell death inducer OXALIPLATINUM.

A-C. Monocyte-derived DCs were loaded with HIEC-6 exposed to PBS or OXA (A) and *B. fragilis* (B) or *P. clara* (C) and were subsequently co-incubated with naïve CD4+ T cells for 7 days. At the end of the incubation, supernatants were assessed for the presence of IFN-gamma by ELISA. Wilcoxon paired comparisons of 6 healthy volunteers, each dot representing one donor.

DETAILED DESCRIPTION OF THE PREFERRED EMBODIMENTS

In the present text, the following general definitions are used:

Colorectal Cancer

Colorectal cancer (CRC), also known as colon cancer or bowel cancer, herein designates any kind and any stage of cancer from the colon or rectum (parts of the large intestine). Proximal colon cancer or proximal colon adenocarcinoma (PCAC), is a particular form of CRC defined by its anatomical localization.

Treatment

As used herein, the terms "treat", "treatment" and "treating" refer to any delay of the progression, reduction of severity, and/or duration of cancer; for example, in CRC, amelioration of quality of life and/or an increase in survival that results from the administration of one or more therapies. This term also designates herein a prophylactic treatment administered to an individual who does not have a CRC but who is at risk of developing this pathology ($MSI^{high}$ individuals)

Anticancer Vaccine

An "anticancer vaccine" herein designates an immunogenic composition which can be administered either to a patient having a CRC to trigger an immune response against the cancer (therapeutic vaccine), possibly in association with other treatments such as a treatment with Oxaliplatin, or to an individual who does not have a CRC but who is at risk of developing this pathology (prophylactic vaccine).

Other definitions will be specified below, when necessary.

As described in the experimental part below, the inventors demonstrated that administration of certain bacteria can compensate dysbiosis and improve the anticancer effects of chemotherapy in an animal model for colorectal cancer. Hence, according to a first aspect, the present invention pertains to the use of a composition comprising live bacteria selected from the group consisting of:
(i) bacteria of the family Erysipelotrichaceae except those of the genus *Solobacterium*,
(ii) bacteria of the family Rikenellaceae,
(iii) bacteria of the class Negativicutes
(iv) bacteria of the orders Selenomonadales and Lactobacillales
(v) bacteria of the species *Bacteroides fragilis*
and mixtures thereof, in the treatment of colorectal cancer (CRC).

According to a particular embodiment, the present invention pertains to the use of a composition comprising live bacteria selected from the group consisting of:
(i) bacteria of the family Erysipelotrichaceae except those of the genus *Solobacterium*,
(ii) bacteria of the family Rikenellaceae,
and mixtures thereof, in the treatment of colorectal cancer (CRC).

According to a particular embodiment of the invention, the composition comprises live bacteria from the genuses *Erysipelatoclostridium, Erysipelothrix* and/or *Turicibacter*.

According to another particular embodiment, the composition comprises live bacteria selected from the group consisting of *Erysipelothrix tonsillarum, Erysipelatoclostridium ramosum, Alistipes onderdonkii* and mixtures thereof.

When performing the invention, the composition can also comprise bacteria selected from the group consisting of *Prevotella copri, Bacteroides* (especially *Bacteroides fragilis*), *Faecalibacterium* (especially *Faecalibacterium prauznitzii*) and mixtures thereof. Other bacteria which can advantageously be included in the composition include *Propionibacterium acnes, Eggerthella lenta* and *Streptococcus anginosus*. Still other bacteria which can advantageously be included in the composition include *S. dentisani* (see FIG. 3Q), *Enterococcus hirae* and *Ruminococcus faecis* (associated to Cluster 1 in FIG. 4A).

According to the invention, the composition is preferably administered to a patient who also receives anticancer chemotherapy such as, for example, an Oxaliplatin-based therapy and/or immunotherapy, such as for example PD-1 blockade and anti-Lag3 Ab. According to a preferred embodiment, the patient receives a neoadjuvant chemotherapy and/or immunotherapy, for example a neoadjuvant Oxaliplatin-based therapy and/or PD-1 blockade and/or anti-Lag3 Ab. Alternatively, the patient can receive an adjuvant Oxaliplatin-based therapy and/or PD-1 blockade and/or anti-Lag3 Ab. The invention thus also pertains to a method of administering immunogenic bacteria (such as those listed above) as an adjuvant in the treatment of CRC, in combination with immunogenic chemotherapy and/or immune checkpoint blockers such as anti-PD1 Ab, anti-PDL1 Ab and anti-Lag3 Ab.

As shown in the experimental part below, the inventors demonstrated that bacteria present in the ileal intestinal compartment play an important part in the evolution of colorectal cancer and in the response of CRC patients to chemotherapy. Therefore, when performing the invention described above, the composition is preferably formulated and/or administered in a way that enables the delivery of live bacteria to the ileum. For example, encapsulated lyophilized bacteria can be administered per os.

According to another aspect, illustrated in the experimental part below, the present invention pertains to a method of obtaining immunogenic enteroids useful for treating a CRC, comprising the steps of
(i) incubating ileal enteroids with a bacterial composition as described above, and
(ii) incubating said ileal enteroids with a cell death inducer (CDI).

The above method can be performed with autologous or heterologous ileal enteroids. Such enteroids can be derived from intestinal stem cells, for example as described by Sato et al. (Nature 2009), starting from fresh (best) or frozen ileal biopsies at the terminal ileum. Examples of CDI that can be used in this method are Oxaliplatin, Doxorubicin, Mitoxantrone or any other immunogenic cell death inducer or combinations well known by the skilled in the art, such as FOLFIRI, FOLFOX and the like.

More precisely, the above method can be performed by first incubating autologous or allogeneic ileal enteroids with live commensals (present in the compositions described above) for 1 hour prior to addition of Oxaliplatin or of another ICD inducer for 3 hours; antibiotics are then added for 1 hour to kill live bacteria and allow subcutaneous or intradermal inoculation of the vaccine.

According to the present invention, immunogenic enteroids useful for treating a CRC can also be obtained by a method comprising the following steps:
(i) incubating ileal enteroids with at least one compound selected from the group consisting of TLR2/TLR4 agonists, IL-1R agonists, anti-CD73 antibodies and anti-CD39 antibodies, and (ii) incubating said ileal enteroids or enterocytes with a cell death inducer (CDI).

When performing the above method, the skilled technician will choose the compound(s) used in step (i) so that it(they) increases the IL-1 and/or ATP release by the enteroids.

The present invention also pertains to an anticancer vaccine for treating a patient having a CRC or at risk of developing a CRC, which comprises immunogenic enteroids obtained by any of the above methods. Such an anticancer vaccine is preferably formulated for subcutaneous or intradermal administration and can comprise autologous or allogeneic immunogenic enteroids.

According to a particular embodiment of the anticancer vaccine according to the present invention, the vaccine comprises enteroids harbouring mutations in DNA repair mechanisms. Indeed, such enteroids (used either autologously or heterologously) have advantageous immunogenic properties. According to a particular embodiment of the anticancer vaccine according to the present invention, the vaccine also comprises enteroids without mutations in DNA repair mechanisms. Indeed, such enteroids (used either autologously or heterologously) have advantageous immunogenic properties against MSS tumors (with low mutational burden).

In what precedes, an individual is considered as "at risk of developing a CRC" if a clinical examination showed early signs of suspected CRC and/or if his/her genetic background or familial history suggests that this individual has a microsatellite instability (MSI). In addition to therapeutic vaccination (for patients having a CRC), prophylactic anticancer vaccination can indeed be advantageously proposed to MSI-$^{high}$ individuals, individuals with Lynch or hereditary non polyposis colorectal cancer (HNPCC) syndrome (3-5%), mutations in DNA mismatch repair genes (MLH1, MSH2, MSH6, PMS2, EPCAM, etc.), familial adenomatous polyposis (APC or MYH gene mutations) such as Gardner or Turcot syndrome (1%) and sporadic CRC with hMLH1 MMR gene methylation.

The invention also pertains to a method of ex vivo differenciating naive T cells into T follicular helper cells and/or Th1 cells, which are useful for treating CRC in a patient. According to this aspect of the invention, the method comprises incubating autologous T helper cells with dendritic cells charged with autologous or allogeneic immunogenic enteroids such as those obtained through one of the methods described above, or with autologous or allogeneic primary intestinal epithelial cells.

The T follicular helper and/or Th1 cells obtained by the above method can advantageously be used for treating or preventing CRC. According to this aspect of the invention, these T follicular helper/Th1 cells are adoptively transferred to the patient. This aspect of the invention is particularly useful for treating or preventing CRC in MSI$^{high}$ individuals, individuals with Lynch or hereditary non polyposis colorectal cancer (HPNPCC) syndrome (3-5%), mutations in DNA mismatch repair genes (MLH1, MSH2, MSH6, PMS2, EPCAM, etc.), familial adenomatous polyposis (APC or MYH gene mutations) such as Gardner or Turcot syndrome (1%) and sporadic CRC with hMLH1 MMR gene methylation, as well as patients harbouring MSS tumors (with low mutational burden).

According to another of its aspects, the present invention pertains to a method (based on the "ileoimmunoscore") for generating a prognostic and/or subtype signature for a patient with CRC, comprising:

(i) assessing expression levels for one or more genes selected from the group consisting of CD3E, AHR, GATA3, TBX21, BCL6, CD4, RORC, FOXP3, FOS, JUN, IL17A, IL27, IL10, IL23A, and IFNG in a sample obtained from the terminal ileum mucosae of the patient, and (ii) comparing the expression levels in the patient with control expression levels, wherein the result provides a prognostic and/or subtype signature for the patient.

According to a particular embodiment of this method, the expression levels for one or more genes selected from the group consisting of CD3E, AHR, GATA3, TBX21, BCL6 is assessed in step (i).

This method is particularly helpful for generating a prognostic in cases of tumor immunoscore IS2 (Galon/Pagès), when the tumor infiltration by CD3, CD8 T lymphocytes in the invasive margin or tumor core is intermediate.

When performing the above method, the person skilled in the art can use the cut-off values described in the experimental part below, provided the same techniques are used to assessing the expression levels of the recided genes. Examples of such thresholds (shown in Table 2 below) are:

CD3E: 63.77;
TBX21: 0.7149;
GATA3: 40.38
AHR: 349.1
RORC: 44.38
IL17A: 0.5202
FOXP3: 0.3871
IL27: 0.352
FOS: 10.54

In the above method, expression level(s) of CD3E, AHR, GATA3, TBX21, RORC, IL17A, FOXP3, IL27 and/or FOS above the control expression level(s) is indicative of a dismal prognosis (shorter time to progression).

Alternatively, the expression levels of all these genes can be used to generate a global molecular signature where global gene expression above the control expression levels is indicative of a dismal prognosis (shorter time to progression). In such a case, the skilled biostatistician will run routine analysis to determine the relevant thresholds.

According to a particular embodiment, the above method is performed by assessing the expression levels of at least one of the recited genes in a sample that has been collected after a neoadjuvant oxaliplatin-based treatment.

According to yet another aspect, the present invention pertains to a method (based on a microbial ileal fingerprint or "ileomicrobioscore") for generating a prognostic and/or subtype signature for a patient with CRC, comprising:

(i) assessing the presence of one or more bacteria selected from the group consisting of Erysipelotrichaceae (especially of genuses *Erysipelatoclostridium, Erysipelothrix* and *Turicibacter*), Rikenellaceae (especially *Alistipes onderdonkii*) *Prevotella copri, Bacteroides* (especially *Bacteroides fragilis*) and *Faecalibacterium* (especially *Faecalibacterium prausnitzii*), Negativicutes, Selenomonadales and Lactobacillales in a sample obtained from the ileum mucosae of the patient, and (ii) assessing the presence of one or more bacteria selected from the group consisting of unclassified YS2, *Clostridium neonatale*, unclassified Lachnospiraceae, unclassified Ruminococcaceae, *Blautia, Christensenella minuta, Bacteroides caccae, Corynebacterium amycolatum, Streptococcus gallolyticus, Bacillus circulans, Ruminococcus gnavus*, uncl. *Phascolarcto-* bacterium, *Bacteroides uniformis*, *Catabacter hongkongensis*, Fusobacteriaceae, Bacteroidaceae except *Bacteroides fragilis*, Tannerellaceae and Prevotellaceae in a sample obtained from the ileum mucosae of the patient, wherein the presence of bacteria recited in (i) is indicative of a good prognosis and the presence of bacteria recited in (ii) is indicative of a bad prognosis.

Alternatively, the above method can be performed by assessing the presence of the recited bacteria in a fecal sample from the patient.

According to a particular embodiment of the above method, the presence of one or more bacteria selected from the group consisting of Erysipelotrichaceae (especially of genuses *Erysipelatoclostridium*, *Erysipelotrhix* and *Turicibacter*), Rikenellaceae (especially *Alistipes onderdonkii*) *Prevotella copri*, unclassified *Bacteroides* and unclassified *Faecalibacterium* is assessed in step (i), and the presence of one or more bacteria selected from the group consisting of unclassified YS2, *Clostridium neonatale*, unclassified Lachnospiraceae, unclassified Ruminococcaceae, *Blautia*, *Christensenella minuta*, *Bacteroides caccae*, *Corynebacterium amycolatum*, *Streptococcus gallolyticus*, *Bacillus circulans*, *Ruminococcus gnavus*, uncl. *Phascolarctobacterium*, *Bacteroides uniformis* and *Catabacter hongkongensis* is assessed in step (ii).

In the case of a proximal colon cancer, the presence of bacteria recited in (i) is indicative of a TIL enriched proximal colon cancer (IS 2-3-4) and the presence of bacteria recited in (ii) is indicative of a TIL negative proximal colon cancer (IS 0-1).

Examples of samples which can be used for performing the above methods are a biopsy of ileum mucosae, ileal fresh mucoase-associated bacterial biofilm biopsy or the ileal mucus, as well as in fecal microbiota which can be used as a surrogate marker of ileal composition.

As disclosed in the experimental part below, the invention also pertains to a method for generating a prognostic and/or subtype signature for a patient with CRC, comprising:
  (i) in vitro assessing the number of cleaved Caspase 3 positive intestinal epithelial cells (Casp3+ IEC) in the ileal crypts by immunohistochemistry, and
  (ii) comparing the number of Casp3+ IEC in the ileal crypts of the patient with a control number of Casp3+ IEC in ileal crypts,
wherein the presence of a higher number of Casp3+ IEC in the ileal crypts of the patient is indicative of good prognosis.

The invention also pertains to a method for generating a prognostic and/or subtype signature for a patient with CRC, comprising:
  (i) in vitro quantitative analysis of the immune cells in ileal intestinal lamina propria and intra-epithelial lymphocytes by immunohistochemistry for the markers CD3, CD4, and BCL6, and
  (ii) comparing the number of immune cells in ileal intestinal lamina propria and intra-epithelial lymphocytes in the patient with control numbers,
wherein the presence of a higher number of immune cells in the ileum is indicative of bad prognosis.

Another aspect of the present invention is a method for generating a prognostic and/or subtype signature for a patient with CRC, comprising in vitro analyzing *B. fragilis*-specific memory CD4+ Th1 response in a blood sample from the patient and comparing it to a control, wherein the presence of a high memory Th1 response towards *B. fragilis* is indicative of a good prognosis.

Other characteristics of the invention will also become apparent in the course of the description which follows of the biological assays which have been performed in the framework of the invention and which provide it with the required experimental support, without limiting its scope.

EXAMPLES

Materials and Methods
Mice

All mouse experiments were performed at the animal facility in Gustave Roussy Cancer Campus where animals were housed in specific pathogen-free conditions or were maintained in isolators for germ-free and FMT experiments.

All animal experiments were carried out in compliance with French and European laws and regulations. The local institutional board approved all mouse experiments (permission numbers: 2014-071-1124 and 2017-020-8964). Female C57BL/6J and BALB/c were purchased from Harlan (France) and Janvier (France), respectively. Mice were used between 7 and 14 weeks of age. Germ-free C57BL/6J mice and Il1ab−/−, Il18−/−, Cd39−/−, Myd88−/−, Tlr2/4−/− and Tlr9−/− (all C57BL/6J genetic background) and WT littermates from the same breeding zones were obtained from the facility located at CDTA (Cryopreservation, Distribution, Typage et Archivage, Orleans, France).

Casp3$^{FL/FL}$; Casp7$^{FL/FL}$; Villin-Cre Tg (Caspase3/Caspase7 IEC double KO) and RIPK3$^{−/−}$; NntMut/Mut (Rip3k KO) were obtained by Dr. Peter Vandenabeele and some experiments were conducted in the animal facility of VIB-UGent Center for Inflammation Research, Ghent, Belgium. Caspase-3$^{FL/FL}$ and Caspase-7$^{FL/FL}$ mice were generated using respectively ES clone HEPD0716_4_G05 and EPD0398_5_E02 (C57BL/6N) from the International Mouse Phenotyping Consortium (IMPC). The neomycin selection cassette was removed using FLPe deleter mice (22). Intestinal specific targeting was achieved by crossing to Villin Cre mice (23).

Antibiotic Treatments

Mice were treated with an antibiotic solution (ATB) containing ampicillin (1 mg/ml), streptomycin (5 mg/ml), and colistin (1 mg/ml) (Sigma-Aldrich), with or without the addition vancomycin (0.25 mg/ml) added in the sterile drinking water of mice. Solutions and bottles were changed 3 times and once weekly respectively. Antibiotic activity was confirmed by cultivating fecal pellets resuspended in BHI+15% glycerol at 0.1 g/ml on COS (Columbia Agar with 5% Sheep Blood) plates for 48 h at 37° C. in aerobic and anaerobic conditions weekly. Duration of ATB treatments were slightly different based on the experimental settings. In brief, to compromise the efficacy of oxaliplatinum with ATB, mice were treated for 2 weeks prior to tumor implantation and continuously throughout the experiment. ATB treatment was discontinued 48 h before oxaliplatin injection in compensation experiments.

Tumor Challenge and Treatment of Tumor Models
Subcutaneous Model of MC38

Syngeneic C57BL/6J mice were implanted with 1×10$^6$ MC38 WT cells subcutaneously and treated intraperitoneally (i.p.) when tumors were 20 to 30 mm$^2$ in size with 10 mg/kg oxaliplatin or vehicle (PBS). The composition of the commensal gut microbiota in the treated and non-treated groups was maintained synchronized by cohousing. Tumor size was routinely monitored every 3 days by means of a caliper.

In indicated experiments, T cell depletion was performed by i.p. treatment with anti-CD4 and anti-CD8 mAbs (GK1.5 and 53-6.72; 200 μg/mouse) or respective isotype controls (LTF-2 and 2A3) (all antibodies from Bioxcell). Depletion treatment started 4 days before OXA and repeated at the same dose every 7 days.

PD-1 blockade was performed by i.p. treatment with anti-PD-1 mAbs (RMP1-14; 200 μg/mouse) or respective isotype controls (2A3) (all antibodies from Bioxcell).

Gut Dissociation to Harvest IEC

Ileum and/or colon were collected and fat tissue, Peyer's patches and feces were removed. Intestines were cut longitudinally and then cut transversally into small pieces into a tube. Pieces were transferred into a new 50 ml tube with 20 ml of IECs medium (PBS, 5% FCS, 5 mM EDTA and 1 mM DTT), vortexed and shaken at 37° C. for 15 min. Cell suspensions were collected in a new tube, filtered with a cell strainer (100 μm), centrifuged, resuspended in PBS, and stored on ice until use.

Enteroid Culture

Crypts were isolated and enriched from the ileum of 8-12 week old C57BL/6J mice as previously described (24) with the following modifications. Briefly, washed pieces of ileum were incubated in crypt chelating buffer (2 mM EDTA in PBS) for 30 minutes on ice. Following the removal of crypt chelating buffer, fragments were vigorously rinsed 3 times with PBS containing 10% FCS and filtered through a 70-μm cell strainer (BD Bioscience). Crypts were pelleted, washed with Advanced DMEM/F12 (ADF) (Invitrogen), resuspended in 1 mL of Matrigel growth factor reduced basement membrane matrix (Corning) and 50 uL drops were pipetted into a 24 well plate. Crypts were overlayed with ADF containing the following: 100 U/mL penicillin G sodium, 100 μg/mL streptomycin sulphate, 2 mM L-glutamine, 10 mM HEPES, 1× N2 supplement, 1× B27 supplement, 50 ng/mL mEGF, 100 ng/mL mNoggin (Peprotech, Hamburg, Germany), N-acetylcysteine (Sigma) (reagents from Invitrogen unless otherwise indicated) and 10% conditioned medium of R-Spondin-1 transfected HEK 293T cells.

Immunizations with IEC Isolated from the Gut

Donor mice were treated with oxaliplatin (10 mg/kg) i.p. for 6 h to induce gut cell death. Control animals were treated with vehicle (PBS) alone. The composition of the commensal gut microbiota in the treated and non-treated groups was maintained synchronized by cohousing. At the end of the treatment, mice were euthanized and the ileum was collected to isolate IEC. One million IECs were then injected s.c. into the left flank of the recipient mice. The procedure was repeated once, 7 days later. Tumor challenge was performed on the right flank 7 days after the last immunization, with doses which obtain 100% of tumor incidence in naïve mice, MC38 ($1\times10^6$ cells), MCA205 ($0.8\times10^6$ cells), CT26 ($1\times10^6$ cells) and 4T1 ($0.3\times10^6$ cells).

In indicated experiments, IEC were pretreated with 100 mM Pyridoxal phosphate-6-azo(benzene-2,4-disulfonic acid) tetrasodium salt hydrate (PPADS, Sigma), 200 μM 2,4-Dinitrophenol (DNP, Sigma), or vehicle for 20 min at 4° C. Treated cells were washed 3 times with cold PBS before injection, or IEC were co-injected with neutralizing anti-HMGB1 Ab (ab18256, Abcam), anti-Calreticulin Ab (NB600-101, Novus Biologicals) or Rabbit IgG Isotype Control (NBP2-24891, Novus Biologicals) at 10 μg per injection.

Immunizations with IEC from Enteroids

Enteroids were treated with 10 μg/ml oxaliplatin for 3 h. IECs were mixed with pasteurized ileal mucus harvested from patient samples as adjuvant, were then injected s.c. ($10^6$ cells) into the left flank of the recipient mice. The procedure was repeated once, 7 days later. Tumor challenge was performed on the right flank 7 days after the last immunization.

*Alistipes onderdonkii, Erysipelatoclostridium ramosum* isolates were isolated in our laboratory from ileal mucus from patients used in vaccination experiments. Enteroids were treated with 10 μg/ml oxaliplatin for 3 h in the presence of $10^6$ bacteria/ml. Bacteria were killed by 1 h gentamicin treatment and immunization performed as described above.

FMT Experiments

Frozen fecal samples were thawed and thoroughly vortexed. Large particulate material was allowed to settle by gravity. 200 μl of supernatant was administered in a single dose by oral gavage. Additionally, an extra 100 μl was topically applied onto the fur of each animal. The resulting gnotobiotic mice were maintained in positive pressurized isolators with irradiated food and autoclaved water. Two weeks after FMT, tumor cells were injected subcutaneously and mice were treated with oxaliplatin or vehicle (PBS) as described above.

Gut Colonization with Dedicated Commensal Species

*Erysipelothrix tonsillarum* and *Solobacterium moorei* were provided by Prof. Ivo Gomperts Boneca, Institut Pasteur, France. *Bacteroides fragilis, Alistipes onderdonkii, Erysipelatoclostridium ramosum, Dialister invisus, Paraprevotella clara* isolates were isolated in our laboratory from ileal mucus from patients used in vaccination experiments. Species were grown on COS plates in aerobic or an anaerobic atmosphere created using anaerobic generators (Biomerieux) at 37° C. for 24-72 hrs. Colonization of ATB pretreated or GF C57BL/6J mice was performed by oral gavage with 100 μl of suspension containing $1\times10^9$ bacteria in PBS. For bacterial gavage, suspensions of $10^9$ CFU/ml were obtained using a fluorescence spectrophotometer (Eppendorf) at an optical density of 1 measured at a wavelength of 600 nm. Three bacterial gavages were performed for each mouse, the first, 24 h before the treatment with oxaliplatin and then 24 h and 72 after the treatment. The efficacy of colonization was confirmed by culturing the feces 48 h after the first gavage. Fecal pellets were harvested and resuspended in BHI+15% glycerol at 0.1 g/ml. Serial dilutions of feces were plated onto COS plates and incubated for 48 h at 37° C. in aerobic and anaerobic conditions. After 48 h, single colonies were isolated and Gram staining was performed. The identification of specific bacteria was accomplished using a Matrix-Assisted Laser Desorption/Ionisation Time of Flight (MALDI-TOF) mass spectrometer (Andromas, Beckman Coulter, France).

Culturomics Analysis

The bacterial diversity of the ileal mucus samples used for the vaccination experiments was explored using a culturomics approach (25, 26).

Each sample was inoculated in aerobic and anaerobic blood culture bottles. Ten-fold serial dilutions of the liquid cultures were subsequently plated on 5% sheep blood enriched Columbia agar (bioMerieux, Marcy l'Etoile, France) and incubated respectively in aerobic conditions for 48 hours and in anaerobic conditions for one week. Obtained colonies were subcultured and routinely identified using a Matrix Assisted Laster Desorption Ionization Time-of-Flight Mass Spectrometer (MALDI-TOF MS, Microflex, Bruker Daltonics, Bremen, Germany) (27).

In case of a failed routine identification, the colony was identified by sequencing the 16S rRNA.

Characterization of Gut Immune Gene Expression Profile by Real-Time Quantitative PCR Analysis Total RNA from gut biopsies was extracted with RNeasy Mini Kit (Qiagen) and then reverse transcribed into cDNA with the SuperScript III Reverse Transcriptase and the RNaseOUT™ Recombinant Ribonuclease Inhibitor (Life Technologies, Saint Aubin, France), in the presence of random primers (Promega, Charbonnieres, France) and the Deoxynucleoside Triphosphate Set, PCR grade (Roche Diagnostics, Meylan, France). cDNA was analyzed by real-time quantitative PCR (RT-qPCR) with the TaqMan method with TaqMan® Gene Expression Assays using the Universal Master Mix II (Invitrogen) according to the manufacturer's instructions using the 7500 Fast Real Time PCR system (Applied Biosystems). Expression was normalized to the expression of the housekeeping gene of Beta 2 Microglobulin by means of the $2^{-\Delta Ct}$ method.

All primers were from TaqMan® Gene Expression Assay (Thermo Fischer). Mouse primers: B2m (Mm00437762_m1), Muc2 (Mm00458299_m1), Cd3e (Mm01179194_m1), Cd4 (Mm00442754_m1), Tbx21 (Mm00450960_m1), Ifng (Mm01168134_m1), Rorc (Mm01261022_m1), Il17a (Mm00439618_m1), Foxp3 (Mm00475162_m1), il10 (Mm01288386_m1), Gata3 (Mm00484683_m1), Il27 (Mm00461162_m1), Il23a (Mm00518984_m1), Bcl6 (Mm00477633_m1), Ahr (Mm00478932_m1), Fos (Mm00487425_m1), Jun (Mm00495062_s1). Human primers: B2M primers: B2M Forward: 5'-GATGAGTATGCCTGCCGTGT-3' (SEQ ID No: 1); B2M Reverse 5'-AATTCATCCAATCCAAATGCG-3' (SEQ ID No: 2); B2M Probe 5'-(6FAM)AAC-CATGTGACTTTGTCACAGCCCAA(TAM)-3' (SEQ ID No: 3), CD3E (Hs01062241_m1), CD4 (Hs01058407_m1), TBX21 (Hs00894392_m1), IFNG (Hs00989291_m1), RORC (Hs01076112_m1), IL17A (Hs00174383_m1), FOXP3 (Hs01085834_m1), IL10 (Hs00961622_m1), GATA3 (Hs00231122_m1), IL27 (Hs00377366_m1), IL23A (Hs00372324_m1), BCL6 (Hs00153368_m1), AHR (Hs00169233_m1), FOS (Hs04194186_s1), JUN (Hs01103582_s1).

Flow Cytometry Analyses

Tumor draining lymph nodes (tdLN) and spleens were harvested at the end of the experiment for the FMT model. Mesenteric lymph nodes (mLN) were harvested 3 days post-oxaliplatin treatment for gut immunology analysis. Lymph nodes and spleen were crushed in RPMI medium and subsequently filtered through a 100 μm cell strainer.

IEC suspensions were obtained from enteroids by means of 3 wash dissociation method, as described above.

In all cases, two million cells were pre-incubated with purified antimouse CD16/CD32 (clone 93; eBioscience) for 20 minutes at 4° C., before membrane staining.

For intracellular staining, the Foxp3 staining kit (eBioscience) was used. Dead cells were excluded using the Live/Dead Fixable Yellow dead cell stain kit (Life Technologies).

Anti-mouse antibodies (and clones) used for phenotyping were: CD3e (145-2C11), CD4 (GK1.5), CD8a (53-6.7), CD45 (30-F11), FOXP3 (FJK-16s), CXCR3 (FAB1685P), CCR6 (140706), CCR9 (W-1.2), PD-1 (29F.1A12), ICOS (11-9942-82), CXCR5 (2G8), CD19 (1D3), iA/iE (2G9), CD11c (N418), CD103 (2E7), CD86 (GL1), FOXP3 (FJK-16s), TNFa (MP6-XT22), (from BD Pharmingen, BioLegend, R&D and eBioscience). Streptavidin PE, Annexin V-APC and Propidium Iodide (PI) were from BD Pharmingen.

Samples were acquired on Cyan ADP 9 colors cytometer (Beckman Coulter) or 13 color Cytoflex (Beckman Coulter) and analyses were performed with FlowJo software (Tree Star, Ashland, OR, USA).

Immunohistochemistry Staining of Cleaved Caspase 3 Expression

FFPE gut sections were deparaffinised and rehydrated through a series of graded alcohols and distilled water. Antigen retrieval was performed by pre-treating sections with 0.01 M sodium citrate buffer (pH 6.0, Diapath) for 30 min in a 98° C. water bath. Endogenous peroxidase activity was inhibited by treating sections with 3% hydrogen peroxidase (#S202386, DAKO) for 10 min. Sections were blocked with IHC/ISH Super Blocking (#PV6122, LeicaBiosystem) for 10 min. The primary polyclonal Rabbit antibody (Ab), Cleaved Caspase-3 (Asp175) (#9661, Cell Signalling, 1 μg/mL) was incubated for 1 h, followed by the secondary Ab, PowerVision Poly-HRP anti-Rabbit IHC Detection Systems (#PV6114, LeicaBiosystem) for 20 minutes. Peroxidases were detected with Di Amino Benzidine-peroxidase substrate kit (DAKO), and counterstained with Mayer's haematoxylin.

Images were acquired as whole slide images (WSI) with a slide scanner Zeiss Axio Scan.Z1 (objective Plan-Apochromat 20×/0.8, 3CCD camera Hitachi HV-F202SCL) and exported from the Zeiss Zen 2 lite software as TIFF images. WSI were processed with using an algorithm developed in Visiopharm Integrator System (VIS) (Visiopharm A/S, Denmark).

For human tissue analysis, QuPath software was used (37). Regions of interest (ROIs) were defined in crypts by both algorithm and hand in each WSI. Total cells and cleaved caspase 3 positive cells within these ROIs were quantified and the percentage of positive cleaved caspase 3 cells and cell density of cleaved caspase 3 positive cells were calculated.

Immunofluorescence Staining, Scanning and Analysis for AHR, CD4 and CD3 Expression in Ileum For multiplexed staining, 3 μm-thick sections of formalin-fixed, paraffin-embedded ileal tissue were stained by automated immunostainer (DISCOVERY ULTRA, Ventana, IGR). Heat-induced antigen retrieval in EDTA buffer (pH 8.0) for 64 minutes at 95° C. was performed. The primary monoclonal mouse anti-human AHR antibody (SantaCruz, A-3, 0.5 μg/mL) was applied on the slides for 1 h at RT, followed by detection using the biotin-free peroxydase system of detection, Discovery UltraMap anti-mouse HRP (Ventana, #760-4313). The Visualization of AHR was accomplished using TSA fluorophore system, Discovery Rhodamine 6G kit (Ventana, #760-244). Heat-induced antigen retrieval in Citrate buffer (pH 6.0) for 10 minutes at 100° C. was performed. Then, the slides were incubated on primary monoclonal rabbit anti-human CD4 antibody (Spring, SP35, 0.5 μg/mL) for 1 hour at 37° C., detected by Discovery UltraMap anti-rabbit HRP (Ventana, #760-4315) and visualized by Discovery Cy5 kit (Ventana, #760-238). Heating step with Citrate Buffer was carried out, as described above. Next, the slides were incubated on primary polyclonal Rabbit anti-human CD3 antibody (DAKO, #A0452, 3 μg/mL) for 1 h at 37° C., detected by Discovery UltraMap anti-rabbit HRP (Ventana, #760-4315) and visualized by Discovery FAM kit (Ventana, #760-243). After the heating step with Citrate Buffer, nuclei were subsequently visualized with Spectral DAPI (Perkin Elmer, FP1490, 1:10).

Fluorescence Analysis

Images displayed in the figures were acquired as whole slide images (WSI) with a slide scanner Zeiss Axio Scan.Z1 (objective Plan-Apochromat 20×/0.8, 3CCD camera Hitachi HV-F202SCL) and exported from the Zeiss Zen 2 lite software as TIFF images. Some of the WSI were processed with using an algorithm developed in Visiopharm Integrator System (VIS) (Visiopharm A/S, Denmark). ROI were defined for each WSI by applying a threshold on the DAPI intensity, and then AHR mean fluorescence intensity was measured in those ROIs.

16S rRNA Gene Sequencing and Analysis

Sequencing. Characterization of metagenomic communities was performed through amplification and sequencing of hyper-variable regions. gDNA extraction, library preparation and sequencing were conducted at GATC Biotech AG (Konstanz, Germany) for cohort 1 and at Genoscreen (Lille, France) for cohort 2. Amplification was performed using region-specific primers that target conserved regions flanking the variable regions, V3-V5 and V3-V4 for cohort 1 and 2, respectively. Sequencing was performed with Illumina MiSeq technology.

Analysis. Total reads were filtered for length (min length=250 bp for cohort 1 and 300 bp for cohort 2) and quality (min quality=20 for both cohorts) and checked for chimeras. A total of 7,951,772 reads was obtained (average 54,839 reads/samples; n=145 samples) for cohort 1 and 1,691,549 reads (average 14,838 reads/samples; n=114 samples) for cohort 2. High quality reads were pooled and grouped into Operational Taxonomic Units (OTUs) based on a 97% similarity threshold with uclust software from QIIME. Estimates of phylotypes richness and diversity were calculated using both Shannon and Simpson indices on the rarefied OTU table (n=4,000 reads for cohort 1 and n=2,000 reads for cohort 2). Singletons were removed and phylogenetic affiliation of each OTU was done by using Ribosomal Database Project taxonomy and performed from phylum to species level.

For the analysis of the expanded cohort, in which 15 new cases were added, we reperfomed sequencing and analysis of all the samples from cohort 2 with the same methods as cohort 1, as described above.

The statistical language R version 3.1.3 was used for data visualization and to perform abundance-based principal component analysis (PCA) and inter-class PCA associated with Monte-Carlo rank testing on the bacterial genera (ade4 library). To decipher the impact of the different clinical parameters on microbiota composition, principal component analyses with the different clinical factors as instrumental variables were computed based on the abundance of the different bacterial taxa for each individual. These inter-class PCA are appropriate to represent a typology displaying the diversity between individual's microbiota and allow highlighting combinations of variables (bacterial phylotypes, or genera, etc) that maximize variations observed between qualitative variables (e.g. clinical parameters). Based on these inter-class PCA, statistical p-values of the link between the different clinical factors with microbiota profiles was assessed using a Monte-Carlo rank test (1000 replicates).

Culturomics and 16S Data Analysis

For each bacterial taxon, a mean frequency was calculated in two groups defined according to a given variable (the response to the vaccination experiment, immunoscore, AhR levels). A relative frequency difference was calculated for each species in order to determine which species were enriched or depleted. Statistical significance of the relative frequency difference was determined using uncorrected chi-square test, comparing the proportion of each taxon in the different groups.

Induction of T Naïve Cells Differentiation by Autologous DCs Charged with Human Intestinal Epithelial Cells Exposed to OXA and Commensals.

CD14+ cells were isolated from PBMC obtained from healthy donors (Miltenyi Kit). Monocytes were differentiated into DCs by adding GM-CSF and IL-4 in the culture medium for 6 days. On day 6, immature DCs were harvested and charged with apoptotic intestinal epithelial cells.

For apoptotic IEC cells preparation, HIEC-6 cells (ATCC) were treated with bacteria 1 h, OXA 3 h, and ATB 1 h, and then left ON. The next morning, Apoptotic cells were harvested, washed 3× in PBS and added to the DC culture.

Naïve CD4 T cells were isolated from the matched donor for each experiment (Miltenyi kit) and added to the DC-IEC culture at a 10:1 ratio. The final co-culture was incubated for 6 days. On day 6, anti-CD3 and anti-CD28 mAb were added to the culture. After 24 h incubation supernatants were assayed for IFNg by ELISA (Biolegend).

Statistics

Data analyses and representations were performed either with the statistical environment R, Microsoft Excel (Microsoft Co., Redmont, WA, USA) or Prism 5 (GraphPad, San Diego, CA, USA). Tumor growth was analysed with dedicated software (https://kroemerlab.shinyapps.io/TumGrowth). Briefly, data was subjected to a linear mixed effect modeling applied to log pre-processed tumor surfaces. p-values were calculated by testing jointly whether both tumor growth slopes and intercepts (on a log scale) were different between treatment groups of interests. In FMT experiments, comparison between the efficacy of OXA for each FMT are derived from the estimated slope between treatment contrasting OXA-PBS for each FMT-treated mice. Contrasts were transformed to be interpreted as % improvement of the tumor size per day of treatment. All reported tests are two-tailed and were considered significant at p-values <0.05. Survival curves were estimated using the Kaplan-Meier product limit method. Univariate or multivariate analyses were performed with the Cox regression model, p-values <0.05 were considered significant.

Hierarchical clustering has been done with the distance 1—Pearson Correlation coefficient and the Ward's agglomeration method. Statistics and graphics were performed using the R software and GraphPad Prism v7.03. All tests were two sided, and p-values <0.05 were considered statistically significant.

Example 1: Importance of the Immune and Microbial States of the Ileal Mucosae in the Prognosis of Advanced PCAC Patients Broad spectrum antibiotics, which sterilize the intestine, reduced the efficacy of OXA against MC38 colon cancer subcutaneously (s.c.) transplanted into C57BL/6J mice (28) (data not shown), and prevented the release of anti-microbial peptides into feces (data not shown), suggesting that OXA concomitantly affected both the gut and the tumor compartments. Driven by these observations, we analyzed whether the microbial composition of the large intestine would influence the efficacy of OXA in treating MC38 tumors. We colonized the intestines of germ free (GF) mice with human colonic content collected from 12 proximal colon adenocarcinoma (PCAC) patients, and three weeks later, inoculated MC38 s.c. While the majority (8/12) of patient feces resulted in antitumor efficacy of OXA comparable to that observed in normal mice reared in specific pathogen-free (SPF) conditions (called henceforth "avatar responders (aR)"), 4 patient feces induced complete resistance to this immunogenic chemotherapy ("avatar non-responders (aNR)") (FIG. 1A-B). Moreover, in response to OXA, aR exhibited a decrease of the ileal TH1/TFH immune tone, defined by low expression of Tbx21, Bcl6, Il27, Gata3, and Ahr (FIG. 1C) but not Il17, Rorc, Il10 and Foxp3 mRNAs, compared to aNR (data not shown). Conversely, there was no significant difference in the expression patterns of these immune genes in colonic mucosae between aR and aNR (data not shown). In parallel, there was a significant decrease in TH17 cells (defined as CD4$^+$CCR6$^+$CXCR3$^-$), while activated TFH cells (defined as CD4$^+$CXCR5$^{hi}$PD1$^{hi}$) selectively accumulated in the tumor draining lymph nodes (tdLN), concomitant to a higher CD8/Treg splenic ratio in aR but not aNR (data not shown). Importantly, tdLN TH17 cells were positively correlated with ileal Ahr gene expression (and not with any other of the ileal immune markers) while tdLN TFH were negatively correlated with ileal Bcl6 gene expression post-OXA (FIG. 1D).

To investigate the possible clinical relevance of this data, we correlated the expression of immune genes in the healthy ileal and colonic mucosae (distant from the site of the cancer) with the microbial communities of ileal, colonic and fecal specimens collected from 138 antibiotic-naïve patients who underwent surgery for a PCAC in 2 independent cohorts. Interclass principle component analyses and Monte Carlo rank test p-values of the clusterization robustness between the clinically relevant parameters and microbial taxons revealed that the ileal microbiota was more closely associated with metastasis at diagnosis than the microbiome from the colonic mucosae or the colon content (data not shown). This analysis was performed in two independent series of patients (n=63 and n=20). As shown in avatar mice, higher ileal (but not colonic) expression of AHR and BCL6 (and to some extent CD4) was observed in PCAC patients with dismal prognosis (stage III-IV) as compared to early stages (FIG. 1E). When focusing the analysis on the cohort of antibiotic-naïve stage III-IV PCAC patients, high ileal (but not colonic) individual expression levels of AHR, TBX21, CD3E and GATA3 were associated with shorter time to progression (FIG. 1F, Table 1).

TABLE 1

Univariate logrank test for gut gene expression and TTP in stage III-IV PCAC patients.

|  | Variable | Hazard ratio | Cut-off | n low | n high | p-value |
|---|---|---|---|---|---|---|
| ILEUM | CD3E | 5.32 | 65.6 | 19 | 18 | 0.018 |
|  | CD4 | 2.52 | 12.42 | 28 | 9 | 0.15 |
|  | TBX21 | 5.21 | 1.503 | 25 | 11 | 0.02 |
|  | IFNG | 0.71 | 0.04298 | 29 | 2 | 0.53 |
|  | RORC | 2.38 | 53.84 | 8 | 29 | 0.13 |
|  | IL17A | 1.88 | 0.07587 | 26 | 3 | 0.24 |
|  | FOXP3 | 3.13 | 1.245 | 27 | 5 | 0.056 |
|  | IL10 | 2.51 | 0.5096 | 28 | 5 | 0.15 |
|  | GATA3 | 4.7 | 9.038 | 18 | 16 | 0.033 |
|  | IL23A | 0.37 | 0.3908 | 25 | 10 | 0.07 |
|  | BCL6 | 6.11 | 32.61 | 19 | 15 | 0.053 |
|  | IL27 | 3.4 | 0.1353 | 23 | 6 | 0.073 |
|  | AHR | 5.26 | 349.1 | 28 | 8 | 0.0044 |
|  | FOS | 3.21 | 3.593 | 32 | 3 | 0.068 |
|  | JUN | 0.55 | 88.37 | 7 | 27 | 0.36 |
| COLON | CD3E | 0.41 | 30.83 | 24 | 15 | 0.11 |
|  | CD4 | 0.43 | 39.75 | 28 | 11 | 0.14 |
|  | TBX21 | 0.39 | 1.751 | 24 | 13 | 0.073 |
|  | IFNG | 0.44 | 0.1388 | 36 | 0 | 0.2 |
|  | RORC | 3.15 | 49.66 | 13 | 26 | 0.027 |
|  | IL17A | 1.86 | 0.0377 | 29 | 2 | 0.26 |
|  | FOXP3 | 1.42 | 1.321 | 31 | 4 | 0.51 |
|  | IL10 | 2.3 | 0.3682 | 33 | 6 | 0.26 |
|  | GATA3 | 1.74 | 31.25 | 22 | 16 | 0.31 |
|  | IL23A | 1.59 | 1.417 | 26 | 13 | 0.38 |
|  | BCL6 | 3.83 | 48.67 | 26 | 13 | 0.062 |
|  | IL27 | 0.56 | 0.02688 | 26 | 2 | 0.36 |
|  | AHR | 1.56 | 517.7 | 26 | 13 | 0.4 |
|  | FOS |  |  |  |  |  |
|  | JUN | 5.49 | 24.35 | 8 | 31 | 0.017 |

PCAC: proximal colon adenocarcinoma; TTP: time to progression.

This initial analysis allowed us to segregate patients with advanced disease (stage III-IV).

We then added 15 new cases to our study (expanded cohort), which resulted in increased segregation of parameters, which can now be applied to all patients (not just stages III-IV) (Table 2).

TABLE 2

Univariate logrank test for gut gene expression and TTP in stage I-IV PCAC patients.

|  | Variable | Hazard ratio | Cut-off | n low | n high | p-value |
|---|---|---|---|---|---|---|
| ILEUM | CD3E | 5.06 | 63.77 | 28 | 50 | 0.004 |
|  | CD4 | 2.22 | 11.06 | 34 | 44 | 0.069 |
|  | TBX21 | 4.44 | 0.7149 | 17 | 61 | 0.029 |
|  | IFNG | 0.52 | 0.1836 | 58 | 20 | 0.222 |
|  | RORC | 3.57 | 44.38 | 34 | 43 | 0.006 |
|  | IL17A | 2.77 | 0.5202 | 67 | 10 | 0.036 |
|  | FOXP3 | 4.76 | 0.3871 | 18 | 48 | 0.021 |
|  | IL10 | 1.83 | 2.342 | 66 | 10 | 0.270 |
|  | GATA3 | 4.32 | 40.38 | 60 | 10 | 0.002 |
|  | IL23A | 0.48 | 0.4294 | 27 | 48 | 0.073 |
|  | BCL6 | 5.88 | 14.27 | 13 | 60 | 0.051 |
|  | IL27 | 10.69 | 0.0352 | 21 | 52 | 0.004 |
|  | AHR | 2.88 | 349.1 | 63 | 13 | 0.017 |
|  | FOS | 2.81 | 10.54 | 64 | 11 | 0.025 |
|  | JUN | 0.48 | 57.1 | 41 | 32 | 0.146 |
| COLON | CD3E | 0.19 | 19.24 | 13 | 67 | 7.08E−05 |
|  | CD4 | 0.50 | 13.51 | 26 | 54 | 0.082 |
|  | TBX21 | 0.34 | 1.751 | 31 | 49 | 0.006 |
|  | IFNG | 0.59 | 0.1291 | 52 | 28 | 0.212 |
|  | RORC | 0.69 | 12.92 | 15 | 65 | 0.411 |
|  | IL17A | 2.24 | 0.0398 | 55 | 24 | 0.047 |
|  | FOXP3 | 0.29 | 0.334 | 10 | 62 | 0.006 |
|  | IL10 | 2.49E+08 | 0.1744 | 15 | 65 | 0.020 |
|  | GATA3 | 0.17 | 3.512 | 13 | 65 | 2.43E−05 |
|  | IL23A | 0.24 | 0.1926 | 10 | 70 | 0.002 |
|  | BCL6 | 0.34 | 28.53 | 12 | 68 | 0.029 |
|  | IL27 | 0.53 | 0.0114 | 28 | 46 | 0.156 |
|  | AHR | 0.22 | 86.66 | 10 | 70 | 0.004 |
|  | FOS | 1.58 | 16.25 | 55 | 25 | 0.251 |
|  | JUN | 2.37 | 18.19 | 12 | 68 | 0.157 |

PCAC: proximal colon adenocarcinoma; TTP: time to progression.

Moreover, the analysis of the global gene signature allowed to classify patients into clusters of good (Cluster 1) or bad prognosis (Cluster 2) by non-supervised hierarchical clustering (FIG. 1G). In Cluster 1, the immune-relevant mRNAs (FOS, RORC, ILA17A, INFG, IL23A, FOXP3, CD3E, IL27, GATA3, BLC6, CD4, AHR, TBX21, IL10 and JUN) were generally less expressed in the ileum, whereas in cluster 2 these ileal mRNAs tended to be expressed at a higher level (FIG. 1G). Surprisingly, there was a mirror image of the transcriptional profile of immune genes in the healthy ileum and colon mucosae (FIG. 1H). Cluster 1 patients exhibited a better time to treatment failure (progression or cancer-related deaths) than those individuals whose ileal signature was classified in cluster 2 (FIG. 1I). This risk stratification was independent of the analyzed cohorts (in which cohort 2 was expanded by the 20 new cases), the pretreatment or not with chemotherapy, the treatment center, tumor stage and MSI-status (FIG. 1G), since it predicted survival for stage IV PCC metastatic patients (FIG. 1J).

The local immune parameters in the ileum affecting patients prognosis was further validated by the immunofluorescence-based detection of total (CD3+) and CD4+ T lymphocytes within the ileal epithelium (EP) or lamina propria (LP), as well as that of CD8+ T cells in the invasive margins of the resected tumor. This analysis revealed the surprising observation of a preponderant anti-correlation (data not shown). Notably, the anti-correlations between TILs and LP cells, was particularly strong for TFH cells. Thus, heavily T cell-infiltrated tumors develop in patients whose ilea tend to contain few T cells.

Based on these correlative multifaceted analyses (including (i) intestinal location, (ii) microbial composition, and (iii) immune-related gene expression profiles), we deduced that the ileal mucosa may represent the intestinal compartment that most closely determines the prognosis of advanced PCAC patients (both its immune and microbial states being of major importance).

Example 2: Protective Role of Intestinal Caspases-3 and -7 in the Immunogenic Cell Death of Ileal Enterocytes Against Colon Cancer—Vaccination with Ileal IEC Next, we immunized naïve C57BL/6J or BALB/c mice using a vaccine composed of normal (non-malignant) ileal IEC harvested from OXA- (or PBS-) treated syngeneic littermates. After two s.c. immunizations 7 days apart, C57BL/6J mice were challenged on the contralateral flank with a lethal dose of syngeneic MC38 colon cancer cells (or irrelevant MCA205 sarcoma that are antigenically different from colon cancers), while BALB/c mice were injected with syngeneic CT26 colon cancer cells (or syngeneic 4T1 breast tumors) on the contralateral flank.

First, we observed that ileal (but not colonic) IEC conferred partial protection against tumor challenge with colon carcinoma but not with sarcoma or breast cancer cells (FIG. 2A-B).

Secondly, IEC from mice pretreated in vivo with OXA were more efficient in protecting against colon cancer growth than were untreated IEC (FIG. 2A-B).

Thirdly, when OXA-exposed ileal mucosae were isolated from mice bearing a conditional, IEC-specific caspase 3/caspase 7 knockout (Casp3/7$^{\Delta IEC}$ driven by Cre recombinase expressed under control of the IEC-specific villin promoter) that abolishes apoptosis, their immunizing potential against MC38 cells was lost (FIG. 2C). In contrast, the deficiency of Ripk3 (Ripk3$^{\Delta IEC}$) did not affect the immunogenicity of OXA-treated ileal enterocytes (FIG. 2C), underscoring the role of apoptosis but not of RIPK3-dependent necroptosis in the immunogenicity of ileal IEC.

Interestingly, the capacity of OXA to trigger the apoptosis-associated cleavage of caspase-3 in vivo was far more prominent in ileal than colonic IEC (FIG. 2D). Moreover, colonic IEC tended to exhibit a reduced proliferation post-OXA (while ileal IEC maintained high Ki67 expression) despite a comparable loss of mucin-producing goblet cells and Muc2 mRNA expression, which stimulated the entry into the cell cycle (data not shown).

We confirmed in vitro that treatment of stem cell derived-small intestine enteroids with OXA triggered a dose-dependent apoptosis culminating in calreticulin cell surface exposure (29) (data not shown). Next, in order to test the biological relevance of various DAMPs released during OXA-induced cell death of ileal IEC, we immunized naïve wild type (WT) C57BL/6J mice with ileal OXA-exposed IEC derived from Cd39, Myd88, Tlr2/Tlr4, Tlr9, Il1αβ or Il18 deficient syngeneic animals or ileal OXA-exposed wt IEC in which DAMPs that are usually associated with immunogenic cell death (ATP, calreticulin and HMGB1) were neutralized by antibodies or pharmacological blockers. The immunogenicity of wt ileal IEC was significantly impaired when TLR2/4 or IL-1R signaling pathways were suppressed or when ATP release was inhibited or purinergic P2 receptors were blocked (FIG. 2E-F), yet did not depend on calreticulin or HMGB1. Of note, the mitotically active Lgr5$^+$ intestinal stem cells were dispensable for the immunogenicity of IEC (data not shown).

Moreover, lack of intestinal caspases-3 and -7 resulted in reduced CD3$^+$ T cells in the tdLN, culminating in the acceleration of the natural tumor progression (data not shown). Intestinal caspases-3 and -7 were required for the OXA-induced trafficking of dendritic cells (data not shown) and activated TFH in the mesenteric lymph nodes (mLN) post-OXA (FIG. 2G) as well as for the anti-tumor efficacy of OXA (FIG. 2H) and TILs accumulation in tumor beds (FIG. 2I).

In locally advanced patients, neoadjuvant chemotherapy precedes surgery, allowing us to estimate the effects of cytotoxicants on various parameters of tumoral or healthy tissues. Immuno-histochemical detection of activated caspase-3 in the ileum of proximal colon cancer patients confirmed that OXA-based neoadjuvant chemotherapy induced local IEC apoptosis, mostly in the crypts (FIG. 2J,K). Ileal crypt caspase-3 activation above the median value tended to be associated with better overall survival in patients benefiting from neoadjuvant chemotherapy, suggesting that this parameter has positive prognostic value (FIG. 2L).

Example 3: The Adjuvant Role of Ileal Microbiota in the Immunogenic Cell Death of Ileal Enterocytes Against Colon Cancer Intrigued by the potential relevance of the ileal microbiome in avatar mice and the development of metastases in patients (FIG. 1), we next analyzed the role of microbe-associated molecular patterns (MAMPs) by comparing the relative immunogenicity of ileal IEC harvested from mice raised in specific pathogen free conditions (SPF) to those reared in a germ free (GF) facility. Of note, OXA-exposed ileal GF-IEC failed to immunize against MC38 compared with ileal SPF-IEC (FIG. 3A). OXA-treated stem cell-derived small intestine enteroids (which are devoid of a microbial ecosystem) actually accelerated MC38 progression compared with untreated enteroids, suggesting that they were tolerogenic (FIG. 3B). Altogether, these findings indicate that ileal IEC exposed to conventional chemotherapy cannot induce a protective anti-cancer immune response in the absence of a favorable microflora, in line with the fact that broad-spectrum antibiotics severely affected the efficacy of OXA against MC38 (28). To directly show that the ileal microbiota can restore the immunogenic properties of local IEC, we supplemented tolerogenic OXA-sensitized ileal enteroids with 10 different ileal mucosae ecosystems harvested from PCAC patients (FIG. 3C-D). Only 6 of these 10 ileal ecosystems were able to restore a relative anticancer protection over negative controls, namely, naïve non-immunized mice, mice only immunized with OXA-treated enteroids or mice immunized with ileal mucosal microbiota without enteroids (FIG. 3D).

To identify bacterial taxa involved in immunogenic demise of ileal IEC, we used various technical approaches (Mi-Seq 16S rRNA gene amplicon sequencing and culturomics) and three strategies (exploring the ileal immune tone, tumor immunoscore and in vivo vaccinations). First, culturomic analyses (25) coupled to 16S amplicon sequencing of gene amplicons of ileal mucosae-associated microbiota in the 6 responding (R) and 4 non-responding (NR) ileal mucosae (FIG. 3D) revealed shared traits among R such as the overrepresentation of Erysipelotrichaceae, (genus *Erysipelatoclostridium*, FIG. 3E) and Rikenellaceae (*Alistipes onderdonkii*, FIG. 3E) family members. Of note, *Faecalibacterium* was also overrepresented in immunizing (versus tolerogenic) ileal mucosae, as confirmed by means of 16S amplicon sequencing in these 10 patient-derived mucosae (data not shown). Secondly, correlative studies aligning the immunoscore of PCAC patients with 16S amplicon sequencing of ileal mucosae-associated microbiota revealed very few taxonomic units contrasting ileal microflora of PCAC patients presenting a favorable (IS>2) versus dismal (ISO-1) immunoscore (10). These taxa included species from the Bacteroidales order, Rikenellaceae family, OTU1040 exhibiting a <93% homology with *Alistipes shahii* in cohort 1 (n=33 PCAC, FIG. 3F and FIG. 6) and unclassified Bacteroidales in cohort 2 (n=17 PCAC, p=0.03) (data not shown). Finally, as interclass principle component analyses and Monte Carlo rank test p values of the clusterization robustness for bacterial composition in 16S amplicon sequencing revealed meaningful differences between AHR-$^{low}$ and AHR$^{high}$ ileal mucosa (data not shown), we found once again that unclass. Erysipelotrichaceae, unclass. Rikenellaceae and unclass. *Faecalibacterium* were associated with low AHR mRNA expression (FIG. 3G and data not shown). Of note, the common bacteria species recovered using both criteria, high AHR expression levels and low immunoscore, associated with tolerogenic ileal mucosae were *Bacteroides uniformis, Ruminococcus gnavus* and unclass. *Pharscolarctobacterium* (FIG. 3I-J); these commensals are negatively correlated with a good prognosis. We conclude that the relative dominance of Erysipelotrichaceae, Rikenellaceae and *Faecalibacterium* in ileal mucosae predicts a low local immune tone, and high abundance of cytotoxic T lymphocytes in tumor beds, both influencing PCAC prognosis (FIG. 3H).

We next examined whether the ileal microbiota could segregate patients classified according to their ileal immune gene expression (expanded cohort). At the level of bacterial families, Volcano plots tended to highlight an overabundance of Erysipelotrichaceae as well as of families/orders of the Negativicutes class (such as Acidaminococcaceae, Selenomonadales unclass.) in cluster 1 patients (with better prognosis than cluster 2 patients) (FIG. 3K). At the species level, there was a significant enrichment in oral *Prevotella* spp. (*P. oralis, P. oryzae*) in cluster 2 patients with dismal prognosis, relative to cluster 1 (FIG. 3L). Conversely, the only bacterium enriched in the favorable cluster 1 (compared with cluster 2) was *Bacteroides fragilis* (FIG. 3L).

Spearman correlation matrices suggested the association of specific bacterial families with the infiltration of tumors by CD3+ and CD8+ T lymphocytes at the invasive margin (IM) or in the core of the tumor (CT) (FIG. 3M). Here again, families belonging to the Negativicutes class (such as Veillonellaceae) were also positively related to density of the CD3+ and CD8+ T cell infiltrate in the invasive margin of the tumor while the proportions of Fusobacteriaceae in the ileum was negatively correlated with the density of the CD3+ and CD8+ T cell infiltrate in the core of the tumor.

Interestingly, the frequency of cleaved caspase-3 positive IECs in ileal crypts was significantly higher in cluster 1 than in cluster 2 patients post-neoadjuvant chemotherapy (FIG. 3N). The frequency of apoptotic crypt cells positively correlated with the proportions of Erysipelotrichaceae (FIG. 3O) but negatively with Fusobacteriaceae (FIG. 3P) in the ileal microbiota of non-neoadjuvant patients. These associations which were obtained both in patients with (n=12) or without prior neoadjuvant therapy (n=30) suggest functional connection between the microbiota, IEC apoptosis and local immunity within the ileum. Further analysis of ileal bacteria in relation to the immunoscore groups revealed a positive association among several species from the Lactobacillales order (Streptococci and Enteroccoci) and the immunoscore group 3 (good prognosis)(FIG. 3Q). The bacterium with the best risk stratification for time to treatment failure was *Bacteroides fragilis* (FIG. 3R).

Of note, several commonalities where found when the fecal microbiota was analysed (FIG. 4A-B), suggesting that several microbial biomarkers of importance for ileal immunity can be found in the colonic compartment. Likewise, fecal microbial composition could be used as a surrogate of ileal composition.

Example 4: Administration of *Alistipes* sp. and Erysipelotrichaceae Restores Oxaliplatin Anticancer Efficacy in Conditions of Gut Dysbiosis Subsequently, we attempted to establish the cause-effect relationship between the relative overrepresentation of Erysipelotrichaceae and Rikenellaceae in responder patients and immunogenic apoptosis of the ileal mucosae by compensating dysbiotic microbiota in aNR mice by oral gavage with several representative isolates of these families. This was done prior to OXA administration in therapeutic settings or before immunizing with vaccines in prophylactic experiments. Of note, *Erysipelothrix tonsillarum* (but not *Solobacterium moorei*, another bacterium from the Erysipelotrichaceae family) improved OXA-mediated anticancer effects against established MC38 cancers in a T-cell dependent manner in the context of ATB- (FIG. 5A-C) or FMT-induced dysbiosis (FIG. 5D-E). Moreover, *Alistipes onderdonkii* (belonging to Rikenellaceae family) and *Erysipelatoclostridium ramosum*, which were cultivated from immunogenic ileal mucosae (FIG. 3E), were efficient in rendering OXA-treated enteroids immunogenic, hence augmenting their MC38 cancer growth-reducing effect (FIG. 5F-G), while the same (and admixed) pasteurized bacteria failed to do so. Finally, the low relative abundance of Erysipelotrichaceae in ileal mucosae was associated with increased risk of presenting with metastases at diagnosis in a cohort of 48 PCAC patients (FIG. 5H-I, data not shown).

Example 5: Administration of *Bacteroides fragilis* and Erysipelotrichaceae Improves Anticancer Efficacy of OXA and Anti-PD-1 Combination in Conditions of Gut Eubiosis We next addressed whether colon cancers that failed to respond to PD1 blockade (alone or combined with OXA)

could become responders after exposure to appropriate "immunogenic ileal commensals" identified above. Hence, we established a cause-effect relationship between the relative overrepresentation of Erysipelotrichaceae and *Bacteroides fragilis* in good prognosis patients and immunogenic apoptosis of the ileal mucosae by compensating a complete (SPF) microbiota in mice by oral gavage with several representative isolates of these families. This was done prior to OXA administration in therapeutic settings. Of note, *Erysipelatoclostridium ramosum* and *Bacteroides fragilis* improved OXA+anti-PD-1 Ab-mediated anticancer effects against established MC38 cancers, while *Prevotella. clara* failed to do so, even aggravated the effects of OXA+PD1 Abs (FIG. 7A-B).

Example 6. Ex-Vivo Generation of Th1 Cells Against Intestinal Epithelial Cells

We, next attempted to analyze whether some individuals are already harbouring memory and protective Th1 immune responses to self stem cells of their crypts and/or commensals that could protect them against a CRC. We established an ex vivo coculture process whereby DCs are exposed to naïve CD4+ T cells after their loading with immunogenic IEC+/−bacteria to differentiate T cells into Th1 cells. This was done by incubating autologous T helper cells with dendritic cells charged with an allogeneic IEC (from the human cell line HIEC-6) which were rendered immunogenic only when previously exposed to *Bacteroides fragilis* and OXA, but not when they were treated with OXA alone or the tolerogenic bacteria *Paraprevotella clara* (FIG. 8). The Th1 cells obtained by this method can advantageously be used for treating or preventing CRC.

Discussion

Altogether, these findings illustrate that the microbiota dictates the ileal immune tone, and shapes the anticancer immune responses elicited by ileal enterocytes succumbing to apoptosis. Caspase 3/7-dependent apoptotic cell death of ileal IEC elicits an immune response against common enterocyte antigens in the mesenteric LN, coupled to the release of some DAMPs (ATP, IL-1) and functional TLR2/4 cell-autonomous signaling, only in the local presence of a bacterial ecosystem that produces MAMPs balancing TH17 (tolerogenic) towards TFH/TH1 (immunogenic) immune responses. Of note, the intestinal apoptosis that is required to induce anticancer immune responses is mechanistically distinct from immunogenic cell death (ICD) (which occurs within the tumor) because it does not require CALR and HMGB1. In response to ileal apoptosis, CD103$^-$ CD11c$^+$ MHC class II$^+$ DC are mobilized to expand activated TFH in mesenteric and tumor draining LN. Given the reduced immune tone of ileal mucosae associated with a parallel decrease of ileal CCL25 expression levels post-OXA (not shown), it is tempting to speculate that TFH activated in the mLN post-chemotherapy have been derived from the inflamed gut, favoring their migration towards the tumor microenvironment. These findings raise the theoretical possibility of a self-reactive T cell-dependent anticancer immunity that could be associated with autoimmune colitis, as observed in some cancer patients treated with chemotherapy, and that can be successfully repressed with antibiotics (30-32). The potential simultaneous phagosomal compartmentalization of apoptotic cells together with commensals and their TLR ligands by antigen-presenting cells in the gut or in the mesenteric LN may provide the opportunity for both self- and non-self-peptides to be concomitantly loaded into MHC class II molecules (33).

This study opens up novel avenues to harness the ileal microbiota and to conceive novel bacterial adjuvants that break self-tolerance against colon cancer antigens.

These findings unveil novel associations between the intestinal microbiota, local immune responses and colon cancer prognosis. Several premises can be discussed based on these data. First, we can infer that right-sided colon cancers may have a worse prognosis because surgeons remove the most antigenic part of the digestive tract, i.e the last 10 cm of ileum, otherwise subject to immunogenic apoptosis and colonized with highly immunogenic natural inhabitants/adjuvants (the ileal mucosa-associated microflora). Consequently and secondly, neoadjuvant chemotherapy of right sided colon cancers may be more beneficial than the one administered in an adjuvant setting because self reactivity and/or molecular mimicry with colon tumor stem cells will allow the elicitation of a long term protective immunity. Thirdly, ilei from patients harbouring genetic defects in DNA mismatched repair (as those described in Hereditary Non Polyposis Colorectal Cancer (HNPCC) for instance) may have a higher propensity to undergo apoptosis (at least with certain compounds) (34-35) and therefore elicit a stronger protective immune response against IEC-derived-self antigens. Fourthly, bacteria from the ileal mucosa-associated which also harbor prokaryotic DNA mismatch repair mechanisms (such as MutS and MutL, and homologues of MSH1 (36) may play a role in regulating the immunogenicity of ileal IEC.

Therefore, generating a biobank of ileal enteroids from colon cancer patients with defined genetic mapping will be instrumental. Establishing biological links between prokaryotic and eukaryotic mismatch repair mechanisms, mucosal immunity and oncogenesis will be key for the future.

REFERENCES

1. C. L. Sears, W. S. Garrett, Microbes, microbiota, and colon cancer. Cell Host Microbe. 15, 317-328 (2014).
2. T. Irrazabal, A. Belcheva, S. E. Girardin, A. Martin, D. J. Philpott, The multifaceted role of the intestinal microbiota in colon cancer. Mol. Cell. 54, 309-320 (2014).
3. A. Belcheva, A. Martin, Gut microbiota and colon cancer: the carbohydrate link. Mol. Cell. Oncol. 2, e969630 (2015).
4. W. Chen, F. Liu, Z. Ling, X. Tong, C. Xiang, Human intestinal lumen and mucosa-associated microbiota in patients with colorectal cancer. PloS One. 7, e39743 (2012).
5. J. Geng, H. Fan, X. Tang, H. Zhai, Z. Zhang, Diversified pattern of the human colorectal cancer microbiome. Gut Pathog. 5, 2 (2013).
6. G. Nakatsu et al., Gut mucosal microbiome across stages of colorectal carcinogenesis. Nat. Commun. 6, 8727 (2015).
7. H. Tjalsma, A. Boleij, J. R. Marchesi, B. E. Dutilh, A bacterial driver-passenger model for colorectal cancer: beyond the usual suspects. Nat. Rev. Microbiol. 10, 575-582 (2012).
8. J. Galon, W.-H. Fridman, F. Pagès, The adaptive immunologic microenvironment in colorectal cancer: a novel perspective. Cancer Res. 67, 1883-1886 (2007).
9. K. Nosho et al., Tumour-infiltrating T-cell subsets, molecular changes in colorectal cancer, and prognosis: cohort study and literature review. J. Pathol. 222, 350-366 (2010).

10. F. Pagès et al., Effector memory T cells, early metastasis, and survival in colorectal cancer. N. Engl. J. Med. 353, 2654-2666 (2005).
11. P. Salama et al., Tumor-infiltrating FOXP3+ T regulatory cells show strong prognostic significance in colorectal cancer. J. Clin. Oncol. Off. J. Am. Soc. Clin. Oncol. 27, 186-192 (2009).
12. G. Bindea et al., Spatiotemporal dynamics of intratumoral immune cells reveal the immune landscape in human cancer. Immunity. 39, 782-795 (2013).
13. A. Sistigu et al., Cancer cell-autonomous contribution of type I interferon signaling to the efficacy of chemotherapy. Nat. Med. 20, 1301-1309 (2014).
14. M. Obeid et al., Calreticulin exposure dictates the immunogenicity of cancer cell death. Nat. Med. 13, 54-61 (2007).
15. F. Ghiringhelli et al., Activation of the NLRP3 inflammasome in dendritic cells induces IL-1beta-dependent adaptive immunity against tumors. Nat. Med. 15, 1170-1178 (2009).
16. L. Apetoh et al., Toll-like receptor 4-dependent contribution of the immune system to anticancer chemotherapy and radiotherapy. Nat. Med. 13, 1050-1059 (2007).
17. J. Alexander et al., Histopathological identification of colon cancer with microsatellite instability. Am. J. Pathol. 158, 527-535 (2001).
18. S. Ogino et al., Lymphocytic reaction to colorectal cancer is associated with longer survival, independent of lymph node count, microsatellite instability, and CpG island methylator phenotype. Clin. Cancer Res. Off. J. Am. Assoc. Cancer Res. 15, 6412-6420 (2009).
19. J. Shia et al., Value of histopathology in predicting microsatellite instability in hereditary nonpolyposis colorectal cancer and sporadic colorectal cancer. Am. J. Surg. Pathol. 27, 1407-1417 (2003).
20. D. Tougeron et al., Tumor-infiltrating lymphocytes in colorectal cancers with microsatellite instability are correlated with the number and spectrum of frameshift mutations. Mod. Pathol. Off. J. U. S. Can. Acad. Pathol. Inc. 22, 1186-1195 (2009).
21. D. T. Le et al., PD-1 Blockade in Tumors with Mismatch-Repair Deficiency. N. Engl. J. Med. 372, 2509-2520 (2015).
22. C. I. Rodriguez et al., High-efficiency deleter mice show that FLPe is an alternative to Cre-loxP. Nat. Genet. 25, 139-140 (2000).
23. B. B. Madison et al., Cis elements of the villin gene control expression in restricted domains of the vertical (crypt) and horizontal (duodenum, cecum) axes of the intestine. J. Biol. Chem. 277, 33275-33283 (2002).
24. T. Sato et al., Single Lgr5 stem cells build crypt-villus structures in vitro without a mesenchymal niche. Nature. 459, 262-265 (2009).
25. J.-C. Lagier et al., Current and past strategies for bacterial culture in clinical microbiology. Clin. Microbiol. Rev. 28, 208-236 (2015).
26. J.-C. Lagier et al., Culture of previously uncultured members of the human gut microbiota by culturomics. Nat. Microbiol. 1, 16203 (2016).
27. P. Seng et al., Ongoing revolution in bacteriology: routine identification of bacteria by matrix-assisted laser desorption ionization time-of-flight mass spectrometry. Clin. Infect. Dis. Off. Publ. Infect. Dis. Soc. Am. 49, 543-551 (2009).
28. N. Iida et al., Commensal bacteria control cancer response to therapy by modulating the tumor microenvironment. Science. 342, 967-970 (2013).
29. L. Galluzzi, L. Zitvogel, G. Kroemer, Immunological Mechanisms Underneath the Efficacy of Cancer Therapy. Cancer Immunol. Res. 4, 895-902 (2016).
30. D. Y. Aksoy et al., Diarrhea in neutropenic patients: a prospective cohort study with emphasis on neutropenic enterocolitis. Ann. Oncol. Off. J. Eur. Soc. Med. Oncol. 18, 183-189 (2007).
31. L. Nesher, K. V. I. Rolston, Neutropenic enterocolitis, a growing concern in the era of widespread use of aggressive chemotherapy. Clin. Infect. Dis. Off. Publ. Infect. Dis. Soc. Am. 56, 711-717 (2013).
32. J. Andreyev et al., Guidance on the management of diarrhoea during cancer chemotherapy. Lancet Oncol. 15, e447-460 (2014).
33. J. M. Blander, R. Medzhitov, Toll-dependent selection of microbial antigens for presentation by dendritic cells. Nature. 440, 808-812 (2006).
34. F. A. Sinicrope, DNA mismatch repair and adjuvant chemotherapy in sporadic colon cancer. Nat. Rev. Clin. Oncol. 7, 174-177 (2010).
35. J. M. Park, S. Huang, D. Tougeron, F. A. Sinicrope, MSH3 Mismatch Repair Protein Regulates Sensitivity to Cytotoxic Drugs and a Histone Deacetylase Inhibitor in Human Colon Carcinoma Cells. PLoS ONE. 8 (2013), doi:10.1371/journal.pone.0065369.
36. M. Banasik, P. Sachadyn, Conserved motifs of MutL proteins. Mutat. Res. Mol. Mech. Mutagen. 769, 69-79 (2014).
37. Bankhead P, Loughrey M B, Fernandez J A, Dombrowski Y, McArt D G, Dunne P D, McQuaid S, Gray R T, Murray L J, Coleman H G, James J A, Salto-Tellez M, Hamilton P W. QuPath: Open source software for digital pathology image analysis. Sci Rep. 2017 Dec. 4; 7(1): 16878.

The invention claimed is:

1. A method of treating colorectal cancer (CRC) in a subject receiving a combined oxaliplatin-based therapy and PD1/PDL1 blockade therapy, comprising administering live bacteria in a way that enables the delivery of live bacteria to the ileum, wherein the bacteria comprise *Erysipelatoclostridium ramosum*, to a patient in need thereof;

wherein administering the live bacteria causes delivery of live bacteria to the ileum of the subject, and increases the anti-tumor efficacy of the combined oxaliplatin-based therapy and PD1/PDL1 blockade therapy against the colorectal cancer (CRC) as compared to the anti-tumor efficacy of the combined oxaliplatin-based therapy and PD1/PDL1 blockade therapy in a subject not receiving the live bacteria.

2. A method of treating colorectal cancer (CRC) in a subject receiving a combined oxaliplatin-based therapy and PD1/PDL1 blockade therapy, comprising administering live bacteria in a way that enables the delivery of live bacteria to the ileum, wherein the bacteria comprise *Bacteroides fragilis*, to a patient in need thereof;

wherein administering the live bacteria causes delivery of live bacteria to the ileum of the subject, and increases the anti-tumor efficacy of the combined oxaliplatin-based therapy and PD1/PDL1 blockade therapy against the colorectal cancer (CRC) as compared to the anti-tumor efficacy of the combined oxaliplatin-based therapy and PD1/PDL1 blockade therapy in a subject not receiving the live bacteria.

3. A method of treating colorectal cancer (CRC) in a subject receiving a combined oxaliplatin-based therapy and PD1/PDL1 blockade therapy, comprising administering live bacteria in a way that enables the delivery of live bacteria to the ileum, wherein the bacteria comprise *Alistipes onderdonkii*, to a patient in need thereof;

wherein administering the live bacteria causes delivery of live bacteria to the ileum of the subject, and increases the anti-tumor efficacy of the combined oxaliplatin-based therapy and PD1/PDL1 blockade therapy against the colorectal cancer (CRC) as compared to the anti-tumor efficacy of the combined oxaliplatin-based therapy and PD1/PDL1 blockade therapy in a subject not receiving the live bacteria.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gatgagtatg cctgccgtgt                                          20

```
<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
aattcatcca atccaaatgc g                                              21

<210> SEQ ID NO 3
<211> LENGTH: 26
<212> TYPE: DNA
<213> ORGANISM: Artificial Sequence
<220> FEATURE:
<223> OTHER INFORMATION: probe

<400> SEQUENCE: 3
aaccatgtga ctttgtcaca gcccaa                                         26
```